United States Patent
Li et al.

(10) Patent No.: US 10,665,886 B2
(45) Date of Patent: May 26, 2020

(54) LI-ION BATTERY CAPACITY AND VOLTAGE PREDICTION USING QUANTUM SIMULATIONS

(71) Applicant: EOCELL LTD, Hong Kong (HK)

(72) Inventors: Jun Li, Zenhai (CN); Deepak Srivastava, San Jose, CA (US); Sang Yang, Palo Alto, CA (US)

(73) Assignee: EOCELL LTD, Hong Kong (HK)

( * ) Notice: Subject to any disclaimer, the term of this patent is extended or adjusted under 35 U.S.C. 154(b) by 0 days.

(21) Appl. No.: 16/191,452

(22) Filed: Nov. 15, 2018

(65) Prior Publication Data

US 2019/0088976 A1   Mar. 21, 2019

Related U.S. Application Data

(62) Division of application No. 12/953,068, filed on Nov. 23, 2010, now Pat. No. 10,177,398.

(51) Int. Cl.
| | | |
|---|---|---|
| *H01M 10/00* | (2006.01) | |
| *H01M 10/052* | (2010.01) | |
| *G16C 10/00* | (2019.01) | |
| *G16C 20/30* | (2019.01) | |
| *G06F 30/20* | (2020.01) | |
| *G06F 111/10* | (2020.01) | |

(52) U.S. Cl.
CPC ......... *H01M 10/00* (2013.01); *H01M 10/052* (2013.01); *G06F 30/20* (2020.01);
(Continued)

(58) Field of Classification Search
CPC ............ G06F 17/5009; G06F 2217/16; G06F 2111/10; G06F 30/20; G16C 10/00; G16C 20/30; H01M 10/00; H01M 10/052; A61K 39/00; C07K 14/005; C12N 2740/14022; C12N 2740/16022; C12N 2740/16222

See application file for complete search history.

(56) References Cited

U.S. PATENT DOCUMENTS

| | | |
|---|---|---|
| 7,338,734 B2 | 3/2008 | Chiang et al. |
| 7,378,189 B2 | 5/2008 | Hagiwara et al. |

(Continued)

OTHER PUBLICATIONS

Arora, Pankaj, Marc Doyle, Antoni S. Gozdz, Ralph E. White, and John Newman. "Comparison between computer simulations and experimental data for high-rate discharges of plastic lithium-ion batteries." Journal of power Sources 88, No. 2 (2000): 219-231. (Year: 2000).*

(Continued)

*Primary Examiner* — Aniss Chad
(74) *Attorney, Agent, or Firm* — Horizon IP Pte Ltd

(57) ABSTRACT

Methods, systems, and computer programs for selecting electrode materials for a lithium battery are presented. In one embodiment, a method includes an operation for developing models for structural and energy analysis of battery stability, safety, cycling and performance, where the models are developed based on a selection of elements and compositions for the electrode materials. Properties of at least on cell performance parameter are estimated, and a cell discharge rate behavior is calculated. Another operation in the method is provided for selecting an electrode material composition based on the estimated properties and the cell discharge rate behavior. The method operations are performed by a computer system that includes a processor.

18 Claims, 17 Drawing Sheets

Hybrid Model Benchmark of half cell of $LiCoO_2$

(52) U.S. Cl.
CPC .......... *G06F 2111/10* (2020.01); *G16C 10/00* (2019.02); *G16C 20/30* (2019.02)

(56) References Cited

U.S. PATENT DOCUMENTS

| | | |
|---|---|---|
| 2006/0154071 A1 | 7/2006 | Homma et al. |
| 2007/0190418 A1 | 8/2007 | Chiang et al. |
| 2009/0157369 A1 | 6/2009 | Li et al. |
| 2009/0256528 A1 | 10/2009 | Greening et al. |
| 2009/0311597 A1 | 12/2009 | Chiang et al. |
| 2010/0021820 A1 | 1/2010 | Ishii |
| 2010/0090650 A1 | 4/2010 | Yazami et al. |
| 2010/0190062 A1 | 7/2010 | Yamamoto et al. |
| 2010/0227220 A1 | 9/2010 | Thackeray et al. |
| 2010/0248033 A1 | 9/2010 | Kumar et al. |
| 2011/0037031 A1 | 2/2011 | Long et al. |
| 2011/0039017 A1 | 2/2011 | Okazaki et al. |
| 2011/0045352 A1 | 2/2011 | Archer et al. |
| 2011/0082024 A1 | 4/2011 | Liu et al. |
| 2011/0111294 A1 | 5/2011 | Lopez et al. |
| 2012/0130690 A1 | 5/2012 | Srivastava et al. |
| 2012/0130692 A1 | 5/2012 | Li et al. |

OTHER PUBLICATIONS

Kim, Ui Seong, Chee Burm Shin, and Chi-Su Kim. "Modeling for the scale-up of a lithium-ion polymer battery." Journal of Power Sources 189, No. 1 (2009): 841-846. (Year: 2009).*

Gerbrand Ceder et al, Computational Modeling and Simulation for Rechargeable Batteries, MRS Bulletin, 619-623, Aug. 2002, www.mrs.org/publications/bulletin.

E. Zhecheva et al, Cation order/disorder in lithium transition-metal oxides as insertion electrodes for lithium-ion batteries*, Pure and Applied Chemistry 74, 1885-1894, 2002, IUPAC.

Kganyago, KR. Thesis, 2004.

Wilmont F. Howard et al, Theoretical evaluation of high-energy lithium metal phosphate cathode materials in Li-ion batteries, Journal of Power Sources 165 (2007), Dec. 30, 2006, pp. 887-891, ScienceDirect, www.sciencedirect.com.

Jiang Fan et al, On the discharge capability and its limiting factors of commercial 18650 Li-ion cell at low temperatures, Journal of Power Sources 117 (2003), pp. 170-178, ScienceDirect, www.sciencedirect.com.

John C. MacDonald et al, Supramolecular Behavior of an Isomorphous Series of Five Bis(2-methylimidazolium 2,6-dicarboxypyridine) M(II) Complexes, Crystal Growth & Design 2004, Jul. 31, 2004, pp. 1203-1209, vol. 4 No. 6, American Chemical Society.

M. Stannley Whittingham et al, Lithium Batteries and Cathode Materials, Chemical Reviews, 2004, Sep. 14, 2004, pp. 4271-4301, vol. 104, No. 10, American Chemical Society.

Ying S. Meng et al, Combining Ab Initio Computation with Experiments for Designing New Electrode Materials for Advanced Lithium Batteries: $LiNi_{1/3}Fe_{1/6}Co_{1/6}Mn_{1/3}O_2$, Journal of the Electrochemical Society, 151, pp. A1134-A1140, 2004.

Hou Xian-Hua et al, "First-Principles Study of Interphase $Ni_3Sn$ in Sn—Ni Alloy for Annode of Lithium Ion Battery", Chinese Physics B, Chinese Physics Society, Colume 17, No. 9 Sep. 2008.

* cited by examiner

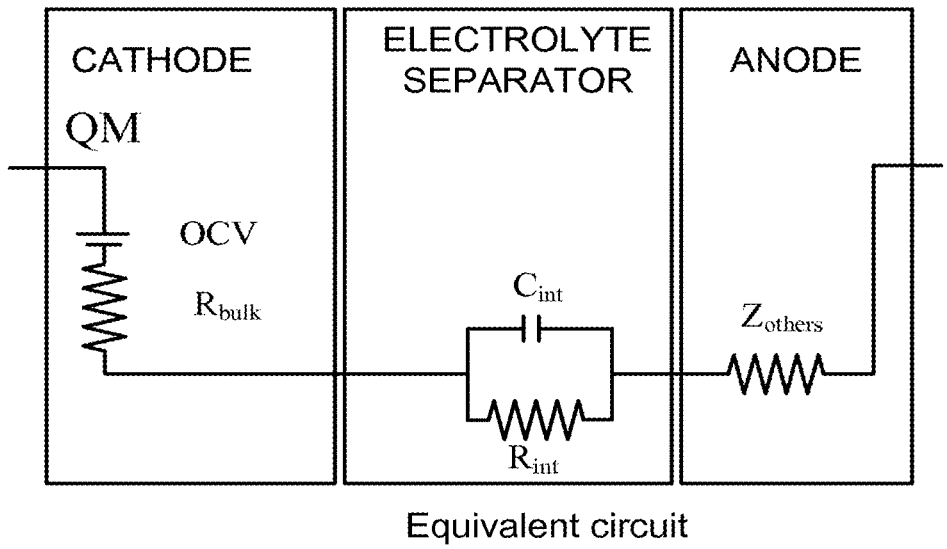
Equivalent circuit
Fig. 6A
| Parameters | OCV (x), $R_{bulk}$(x) | $Z_{others}$ |
|---|---|---|
| Relation to cathode | Bulk | No relation |
| Dependence on Li concentration (x) | Strong | No dependence |
Fig. 6B
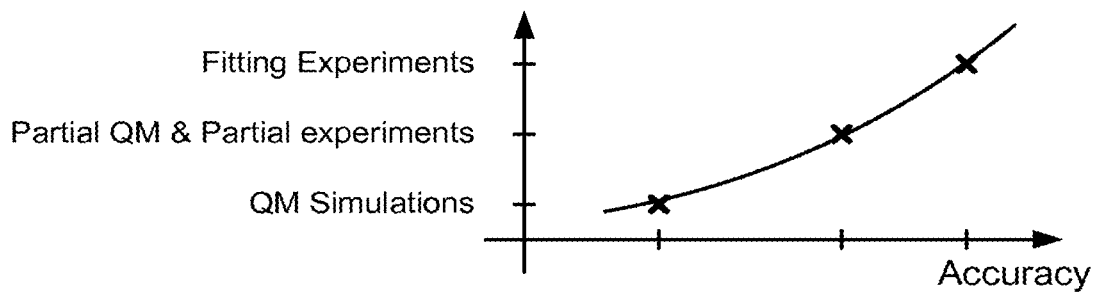
Fig. 6C

Fig. 7A  Fig. 7B

Discharge Curve

Cathode: WM half cell of LCO discharging curve

Anode: half cell of graphite discharging curve

Full cell: LCO + Graphite

LI-ION BATTERY CAPACITY AND VOLTAGE PREDICTION USING QUANTUM SIMULATIONS

CROSS REFERENCE TO RELATED APPLICATIONS

This application is a divisional application claiming the benefit of co-pending U.S. patent application Ser. No. 12/953,068 filed on Nov. 23, 2010, which herein incorporated by reference in its entirety for all purposes. Furthermore, this application is related to U.S. patent application Ser. No. 12/334,170 filed Dec. 12, 2008, and entitled "FAST AND HIGH THROUGHOUT SEARCH ENGINE FOR MATERIALS FOR LITHIUM-ION BATTERIES USING QUANTUM SIMULATIONS;" U.S. patent application Ser. No. 12/953,080 filed on the same day as the instant application and entitled "SIMULATED X-RAY DIFFRACTION SPECTRA FOR ANALYSIS OF CRYSTALLINE MATERIALS;" U.S. patent application Ser. No. 12/953,062 filed on the same day as the instant application and entitled "HYBRID MODEL FOR DISCHARGE PROFILE PREDICTION OF BATTERY ELECTRODE MATERIALS USING QUANTUM SIMULATIONS;" U.S. patent application Ser. No. 12/953,048 filed on the same day as the instant application and entitled "QUANTUM-SIMULATIONS DATABASE AND DESIGN ENGINE FOR DEVELOPMENT OF LITHIUM BATTERIES," all of which are incorporated herein by reference for all purposes.

BACKGROUND

1. Field of the Invention

The invention relates to the development of Li-ion batteries, and more specifically, to the use of quantum simulations and modular analysis of composite solid solution cathode and alloyed anode materials structures for rapid development of Li-ion batteries.

2. Background of the Invention

Advanced batteries substantially impact the areas of energy storage, energy efficiency, hybrid and plug-in electric vehicles, power tools, laptops, cell phones and many other mobile electronics and entertainment devices. Rechargeable lithium-ion batteries offer the highest energy density of any battery technology and, therefore, are an attractive long-term technology that now sustains a billion-dollar business. At the materials level, over the last 30 years the major 10 improvement in the performance of lithium batteries has been achieved through the discovery of new lithium cathode materials. $LiTiS_2$ was the first commercialized cathode material for lithium batteries in the 1970s. $LiCoO_2$ is currently the most active cathode material used in lithium-ion batteries since its discovery in the early 1990s.

However, the safety and high cost of cobalt significantly limits its application to the emerging high capacity and high power battery markets. Additionally, the low charge and discharge rate capability is a well-known problem of lithium-ion batteries. Recent efforts in both industrial and academic communities to overcome these limitations have been focused on compositional modification of $LiCoO_2$, mainly by infusion with other transition metal elements, or new architectures for advanced composite materials for cathodes.

There has been an interest in the development of an advanced anode using alloyed materials since commercialization of the graphite anode accompanying the $LiCoO_2$ cathode in the 1990s. Alloyed materials for an advanced anode and composite materials for an advanced cathode are the mainstream approach for next generation Li-ion battery technology. Both have the same nature of disorder, in contrast to the well-defined crystalline structures of $LiCoO_2$ and graphite.

Searching for new materials by empirical experimental efforts is time-consuming and expensive. Significant efforts are currently underway, mainly in the academic community and Department of Energy laboratories to use quantum simulations (QS) on high performance computers to accelerate the search for new and better materials for the battery industry. Quantum simulations, based on the first-principles density functional theory (DFT) or its equivalent, provide reliable computer simulations to predict on atomic-scale the properties of currently known battery materials for cathodes, anodes and electrolytes. The accuracy of the QS-based predictions of materials properties has been proven in a broad range of applications (e.g., semiconductors and pharmaceuticals.)

QS-based first principle DFT methods provide reliable information about the materials structures and the energy associated with making structural, electronic, and ionic changes in the materials. The typical QS methods, however, are time consuming, CPU intensive, and do not scale well with the size of the system simulated using QS. Few selected cases of Li-ion battery electrode materials in the layer oxide, spinel, and olivine class have been investigated using DFT-based QS (QS-DFT). The typical QS-DFT methods for thousands of compositional variations in the layer oxide, spinel, olivine, and their composites are not feasible with the current technology.

SUMMARY

Embodiments of the present invention provide methods and computer programs for predicting lithium battery properties. It should be appreciated that the present invention can be implemented in numerous ways, such as a process, an apparatus, a system, a device or a method on a computer readable medium. Several inventive embodiments of the present invention are described below.

In one embodiment, a method for predicting lithium battery properties includes operations for selecting candidate structures for the battery, and for obtaining a plurality of delithiated structures of the candidate structures with different lithium concentrations. The quantum mechanical (QM) energies of the delithiated structures are calculated, and a functional form is developed to obtain a voltage of the lithium battery. The functional form is a function of the lithium concentration and is based on the QM energies of the delithiated structures. Further, the capacity of the lithium battery is calculated based on a selected lithium concentration, where the functional form returns a cut-off voltage of the lithium battery when the lithium concentration is equal to the selected lithium concentration.

In another embodiment, the calculating of the capacity further includes making the capacity equal to the selected lithium concentration times a maximum theoretical capacity of the candidate material structure of the selected lithium concentration. In yet another embodiment, the method further includes an operation—for calculating a nominal voltage of the lithium battery as an average between the cut-off voltage of the lithium battery and a first parameter in the functional form. In another embodiment, the functional form is a curve defined by the formula $V(x)=V_{oc}+C(x-1)+D(x-1)^2+E(x-1)^3$, where x is the lithium concentration. In another embodiment, higher order terms with successively lower contribution to the capacity are also included in the formula for V(x). In yet another embodiment, the functional form is a line defined by the formula $V(x)=V_{oc}+C(x-1)$, where x is the lithium concentration and the first parameter is $V_{oc}$.

In one embodiment, a method includes an operation for adjusting the functional form to compensate for underestimation of voltages of a given class of material compared to experimentally obtained values of the same class of material. In yet another embodiment, a method includes repeating calculations of QM energies for additional lithium concentrations, and iterating the calculation of the capacity with the additional lithium concentrations. In another embodiment, the calculating of the QM energies further includes determining whether the QM energy for a particular lithium concentration is already available, performing a simulation of the QM energy for the particular lithium concentration when the QM energy is not available, and adding results of the simulation to a database of QM energies.

In one embodiment, the calculating of the QM energies is performed using density functional theory (DFT)-based QM methods, semi-empirical methods, or empirical methods. In another embodiment, electrochemical properties are calculated using a Halpin-Tsai combination of the electrochemical properties of individual structures obtained via QM energies, or the electrochemical properties are calculated using a weighted Halpin-Tsai combination, according to the different roles of individual structures obtained via QM energies in a composition of the battery.

In another embodiment, a computer program embedded in a non-transitory computer-readable storage medium, when executed by one or more processors, is provided for predicting lithium battery properties. The computer program includes program instructions for selecting candidate structures for the battery, and program instructions for obtaining a plurality of delithiated structures of the candidate structures with different lithium concentrations. Additional program instructions calculate the quantum mechanical (QM) energies of the delithiated structures, and to develop a functional form to obtain a voltage of the lithium battery. The functional form is a function of a lithium concentration and is based on the QM energies of the delithiated structures. The computer program further includes program instructions for calculating the capacity of the lithium battery based on a selected lithium concentration, where the functional form returns a cut-off voltage of the lithium battery when the lithium concentration is equal to the selected lithium concentration.

Other aspects of the invention will become apparent from the following detailed description, taken in conjunction with the accompanying drawings, illustrating by way of example the principles of the invention.

BRIEF DESCRIPTION OF THE DRAWINGS

The invention may best be understood by reference to the following description taken in conjunction with the accompanying drawings in which:

FIG. 6A illustrates the hybrid model for a typical half cell setup that consists of a cathode, an electrolyte separator, and an anode, according to one embodiment.

FIG. 6B summarizes the impact of the parameters of the equivalent circuit of FIG. 6A.

FIG. 6C illustrates the accuracy level of predicted battery properties based on the amount of experimentation or simulation performed.

FIGS. 7A-7C illustrate the benchmarking of the hybrid model for a half cell of $LiCoC_2$, according to one embodiment.

DETAILED DESCRIPTION

Embodiments of the invention provide methods, systems, and computer programs for a fast and high-throughput design engine platform for the selection of quantum simulated Li-ion battery materials that conform to requirements of structure, safety, cycling ability, capacity, and power variation. The determination of the materials is based on quantum simulations where a database of modular elements for the simulations is kept for fast search and selection of the best structures for Li-ion batteries. It will be obvious, however, to one skilled in the art, that the present invention may be practiced without some or all of these specific details. In other instances, well known process operations have not been described in detail in order not to unnecessarily obscure the present invention.

In one embodiment, the system creates all possible compositionally different structures of the layered oxide, spinel, and olivine-type electrode materials, as well as their solid solutions and mixed variants such as composite materials. In another embodiment, the platform provides screening of all the created materials structures according to their relative performance for providing better safety, longer cycle life, higher nominal voltage, higher capacity, and higher rate or power for a Li-ion battery. The platform technology provides fast screening for safety, cycling ability, voltage, capacity, and rate or power characteristics of all the created structures from the quantum simulated building blocks in the database. Further, the platform provides incrementally higher accuracy and fine grain screening on a short list of candidate materials for safety, cycling, nominal voltage, capacity, and power.

A battery material-to-cell system level design and development engine, referred to herein as the development engine, is provided that allows a user to select inputs (e.g., composition for simulation), request computations, generate capacity information, specify hierarchical screening criteria, etc. The development engine includes an easy-to-use Graphical User Interface (GUI) to accomplish these tasks. Further, the development engine enables the screening or filtering of a wide variety of positive and negative electrode materials which are then used with given electrolyte materials for system level design of all cylindrical and prismatic Li-ion battery cells. The architecture and the implementation of the quantum-simulation-driven material search and design platform allows quantum simulated atomic variation in the electrode materials properties to be directly linked to the performance of Li-ion battery cells for better safety, longer cycling ability, higher nominal voltage, higher capacity, etc.

Figure 1:
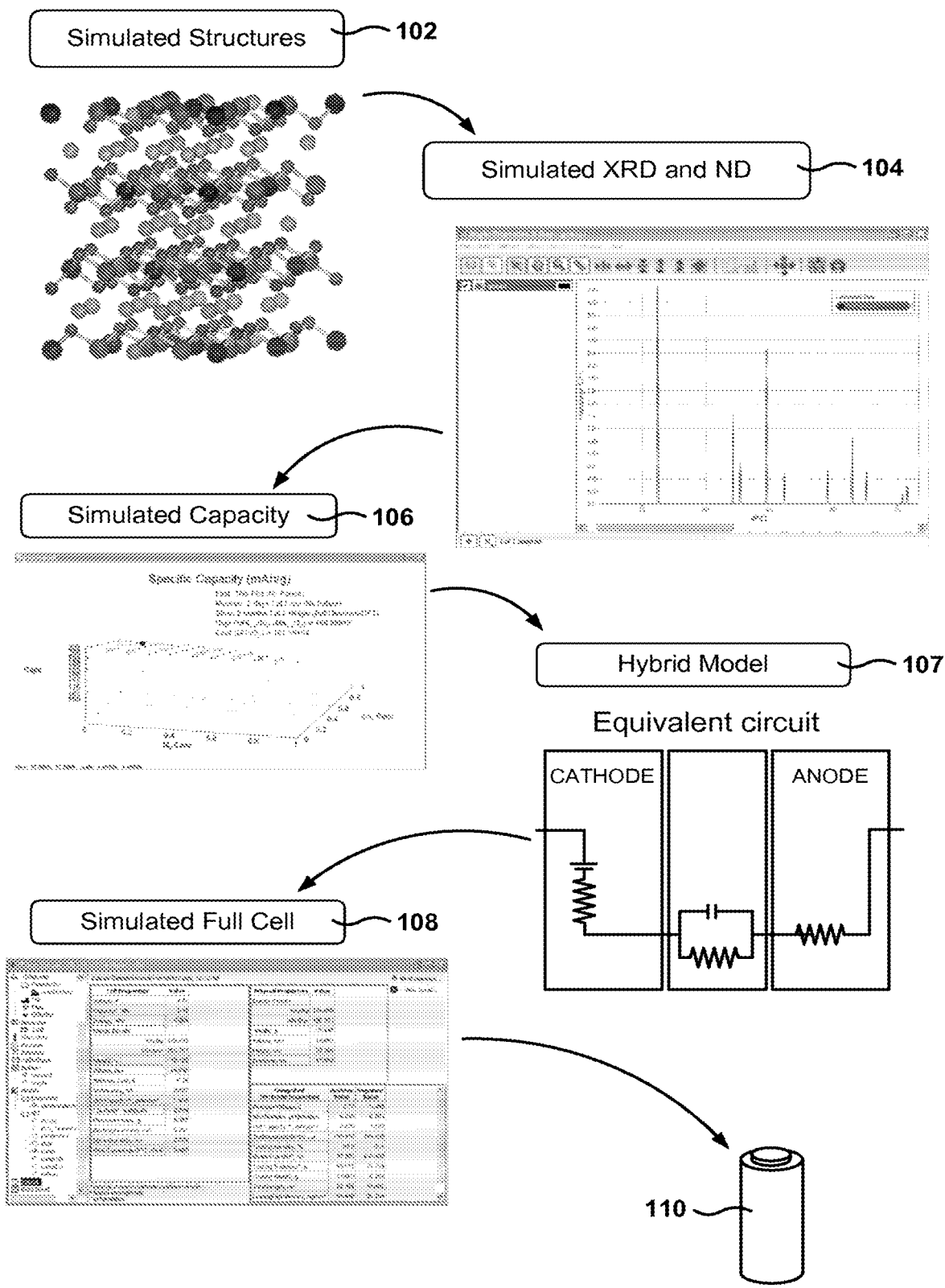
FIG. 1 illustrates at a high level the process for the fast design of Li-ion batteries, according to one embodiment.

FIG. 1 illustrates at a high level the process for the fast design of Li-ion batteries, according to one embodiment. In operation 102, the properties of simulated structures are calculated based on the properties of quantum-simulated structures kept in a database and based on the input materials class, the candidate materials, and the compositional ratios of the elements chosen. A structural analysis 104 of the simulated structures is performed via X-ray diffraction (XRD) or Neutron Diffraction (ND) software tools that obtain the simulated XRD and ND spectra of all the defected and non-defected structures.

Based on the most probable group of candidate structures from operation 104, the method obtains the simulated capacity 106 for the selected structures by doing additional simulations of delithiation of the candidates, unless the information on the delithiation candidates already exists in the database. Delithiation is the extraction of Li ions from the lattice of the cathode material and insertion into the lattice of the anode of a Li ion battery. In operation 107 a hybrid model approximation is used to calculate half cell discharge curves. The model used is called a hybrid model because it is capable of combining designed electrode material quantum simulation data with experimental data for electrolyte and counter electrode effects.

In operation 108, the data for a simulated fuel cell is obtained. Operation 108 runs a system level battery cylindrical tool or a prismatic cell design tool, both of which are part of the development engine. The design engine gets as one of the inputs the simulated half cell discharge curves calculated with the hybrid model in operation 107. After validating the results, one or more materials are selected for testing in a Li-ion battery 110.

Generally, the speed of the simulations is inversely related to the accuracy of the results, i.e., the longer the program runs performing the simulations, the more accurate results the program will produce. Obviously, the more complex algorithms require longer running times. Different types of simulations and models have different levels of complexity and running time, which result in differences in the accuracy of the results for the simulations. The linearized mixing, weighted mixing, and traditional composite based mixing methods (e.g., Halprin-Tsai model extended to multi-component elemental systems) give a very fast approximation to the true solution and are used for coarse grain searching and screening of the compositional and structural variations in a large range of structures and properties. The intermediate range mixing methods are based on a mapping of the localized QS-DFT charges and energies from the modular building blocks to the larger structures. These intermediate range mixing methods are used for fine grain screening and searching in a short-listed range of structures identified with the faster methods. The final validation is obtained either via full QS-DFT simulations of the few selected structures or via synthesis performance evaluation of the chosen compositions and morphologies through experimentation. A validation by full QS-DFT typically takes a few days to few weeks per model (among hundreds to thousands of possible stoichiometric variations per composition) depending upon how much previous data is available from the database via the simulations, or few weeks per composition using full experimental synthesis and characterization methods.

Figure 2:
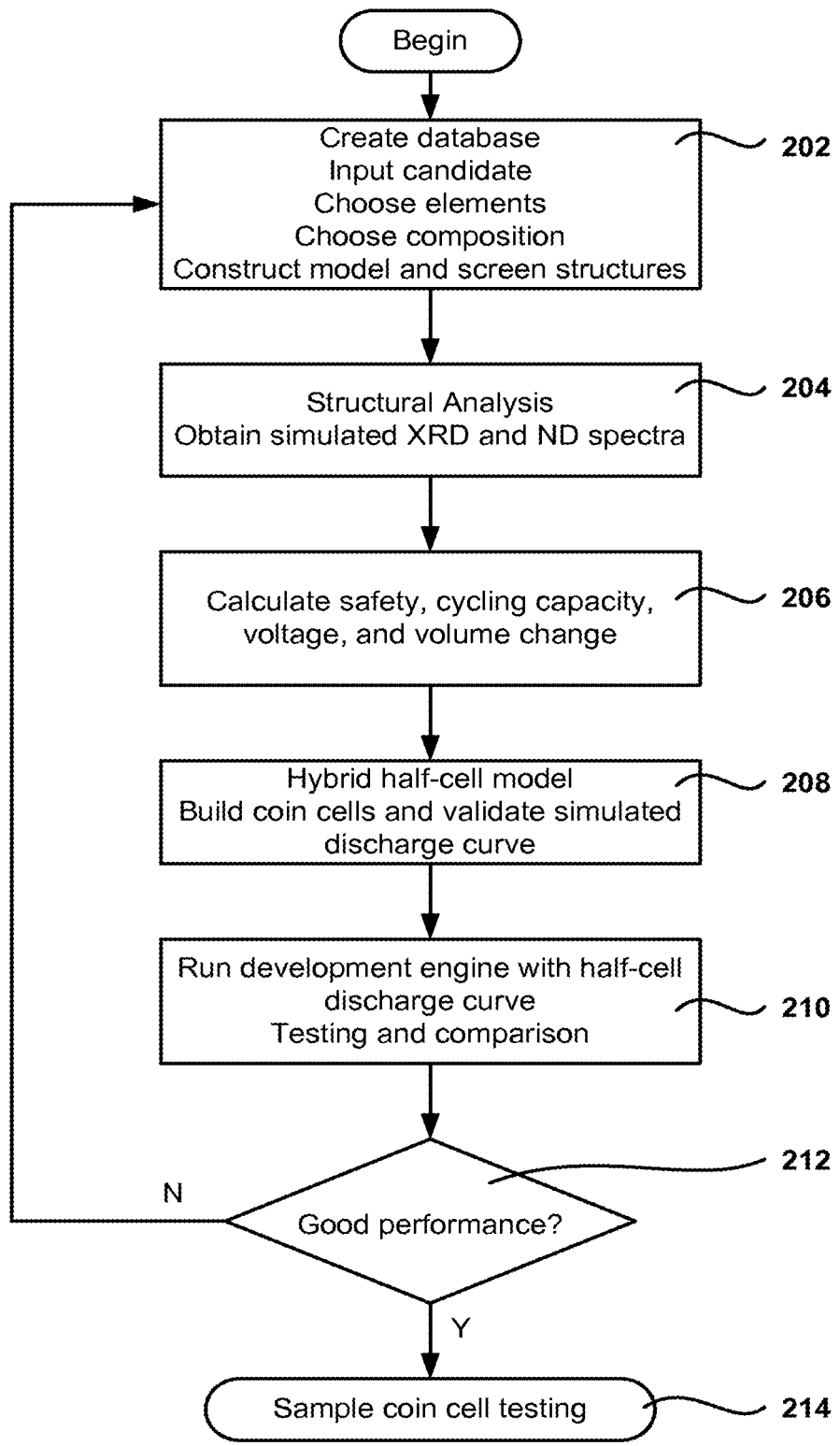
FIG. 2 is a high level flow chart of a method for testing and selecting Li-ion battery materials, structures, and compositions, in accordance with one embodiment.

FIG. 2 is a high level flow chart of a method for testing and selecting Li-ion battery materials, structures, and compositions, in accordance with one embodiment. The battery development system includes a database of quantum-simulated structures and related properties. The structures in the database are used as modular "Lego™-like" building blocks for battery electrodes and electrolyte materials used in Li-ion batteries. Embodiments of the invention provide a set of physics-based design rules and models for creating and screening solid-solutions and composite models of complex materials with the goal of achieving better safety, longer cycle life, higher nominal voltage, increased capacity, greater power, etc.

A computer program for battery development, referred to herein as the development engine, includes a GUI that enables the user to make changes in the quantum or atomistic levels of the new battery electrode and electrolyte materials incorporated into system level cylindrical and prismatic cell design. Through the GUI the user selects the parameters related to the different possible simulations and combinations of materials.

The database of modular building blocks is continuously updated and expanded using QS-DFT, semi-empirical or empirical classical potential based methods. Further, the design rules and development models provide the relative characterization of safety, cycling-ability, volume changes, nominal voltage, capacity, and discharge curves of complex composite and solid solution battery electrode materials against benchmark materials.

A method 202 for creating a quantum simulation database of modular building blocks of materials and creating and screening structures of larger scale complex materials is described in U.S. application Ser. No. 12/334,170, filed Dec. 12, 2008, and owned by the assignee of the present application (the pending '170 application). More details of method 202 are described below with reference to FIG. 3A.

Embodiments for determining the structure of a composite or solid solution material for an electrode in a lithium-ion battery are presented. More particularly, such materials are used in a cathode. Transition metal atoms that may be used for the composite or solid solution materials include, but are not limited to, Sc, Ti, Zr, V, Nb, Cr, Mo, W, Mn, Fe, Co, Ni, Cu, Pd, Pt, Te, Ru, Rh, Cd, Ag, Au, Y and Zn.

The methods described herein may also be used, for example, for determining the structure of an alloyed anode material in a lithium-ion battery. In such methods for alloyed anode materials, an active backbone element in the structure of the alloyed anode material, like the transition metal atoms in the composite or solid solution material for a cathode, are substituted. Active backbone elements for the 20 alloyed anode material may include, but are not limited to, B, Al, Ga, C, Si, Ge, Sn, N, P, Sb, Bi, O, S, Se, Te, Zn, Cu, Ag and Au.

X-ray diffraction (XRD) yields the atomic structure of materials and is based on the elastic scattering of X-rays from the electron clouds of the individual atoms in the system. In operation 204, the quantum simulated relaxed and defected structures of battery materials are generated by the development engine. The coordinates of these structures are used as inputs for an integrated XRD/ND tool within the development engine which returns the simulated XRD/ND spectra of QS simulated materials structures. In one embodiment» the experimental characterization of materials structures synthesized in the laboratory, which takes the spectrum of a synthesized material, is compared to the observed peaks of known crystalline structures to characterize the structure of the synthesized material. More details of operation 204 are described below with reference to FIG. 3D.

In operation 206, a fast evaluation of material characteristics is 10 performed. The characteristics include safety, cycling ability, capacity, voltage, volume change on charge discharge, etc. More details of operation 206 are described below with reference to FIG. 3B.

Operation 208 involves building coin cells and validating the simulated discharge curves using a hybrid half cell model. More details of operation 208 and the hybrid half cell model are given below with reference to FIGS. 3C and 6A-6B. Further, operation 210 includes running the development engine to design and test via the simulation of the electrodes for cylindrical and prismatic full cells using the simulated half cell discharge curves previously obtained, the development engine performs the simulation of half cell discharge curves for the QS designed electrode active material and the testing of the designed electrode with user specified parameters against standard or customized counter electrodes and electrolytes.

The obtained performance for the selected and designed structures is checked in operation 212 to determine whether the performance meets the requirements for the materials. If the requirements are met, the method continues to operation 214 where an actual coin cell is built and tested to validate the simulation results. If the requirements are not met, the method returns to operation 202.

FIGS. 3A-3D present an embodiment of a method for screening and optimizing battery materials for Li-ion batteries. As previously described, the pending '170 application describes in detail methods for creating a database of quantum simulated building blocks and methods for screening or filtering the chosen or designed candidate materials structures. The screened or filtered structures are those that have been classified such that structures in the same classification have the same or similar properties. From all possible combinations of structures derived from a specific query, the structures are ranked according to an energy criteria, and the structures with the highest ranking for stability are selected for further analysis. The pending '170 application presents methods and systems for determining the structure of a composite or solid solution material for an electrode of a lithium-ion battery. In one method, a building-block database of hypothetical structures containing only one transition metal atom is constructed by use of quantum simulation. Then, a composite model set of structures containing two or more transition metal atoms is constructed by calculating a linear average of parent components from the building-block database of hypothetical structures to determine lattice constants and atomic coordinates of candidates. The composite model set is screened or classified into one of a plurality of possible subsets using a local order matrix such that composite models in the same subset share a property in local transition metal ordering. Further, a representative model from each subset is selected and a quantum simulation on the representative model is performed to determine the structure and properties of the material.

Figure 3A:
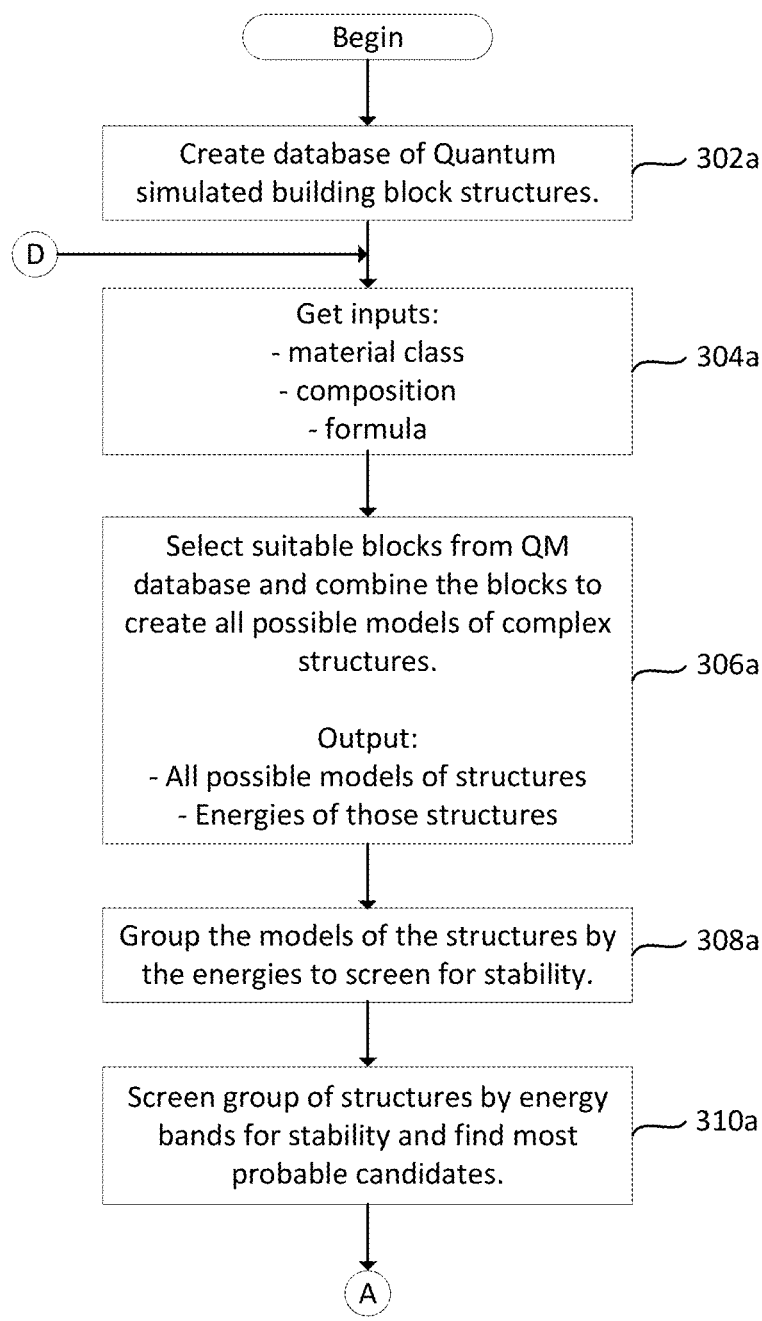
FIGS. 3A-3D present an embodiment of a method for screening and optimizing battery materials for Li-ion batteries.

Referring now to FIG. 3A, in operation 302a, the building block database is created. The building blocks are models, where each building block model could be a real or a hypothetical structure containing one or more transition metal atoms in their crystal unit cells. The simplicity of the model makes accurate QS search of new architectures possible in a timely manner. For example, replacing Co in layered (or spinel) $LiCoO_2$ with another transition metal element forms a new constitutive crystal to be used later as a component of solid solution models. The building blocks may or may not be physically feasible or synthesized in the laboratory, and yet could serve as the computationally derived building blocks to determine the search criteria and domain of more complex solid solutions or composite materials that are feasible and that can be synthesized for lithium-ion battery applications.

The database of such modular building block materials structures and the related properties includes QS-DFT simulated lattice constants, atomic configurations, relative energies, charge distributions, volume changes, and solubility for lithiated and delithiated, oxygenated and oxygen extracted, and cation disordered states of the same. In one embodiment, a complex solid-solution or composite material is broken up to generate a library of QS-DFT simulated modular building blocks such that many of the desired structural, safety, and electrochemical performance characteristics can be simulated on the fly using the physics based hierarchical models and design rules described below.

Figure 3B:
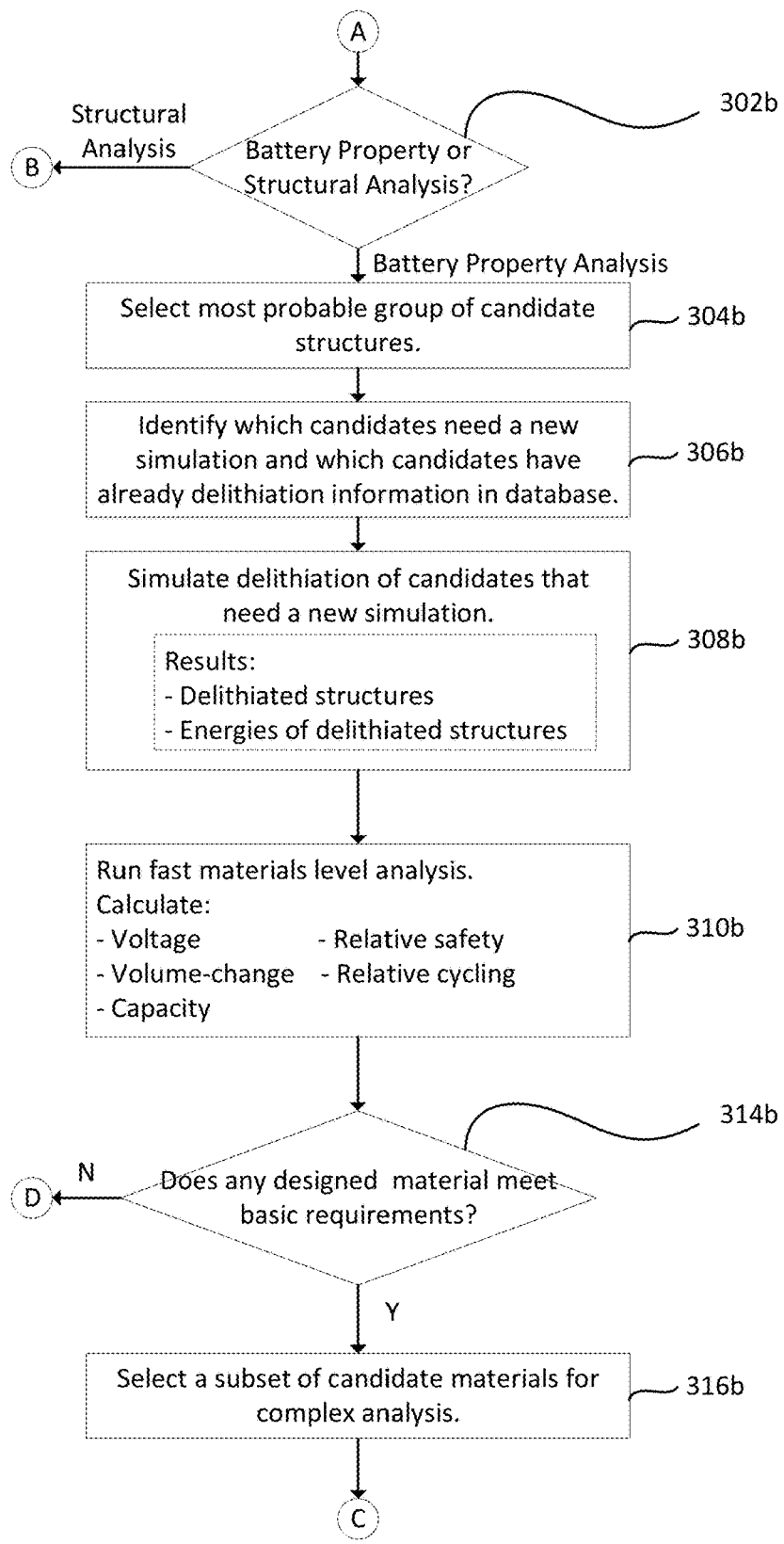
Figure 3C:
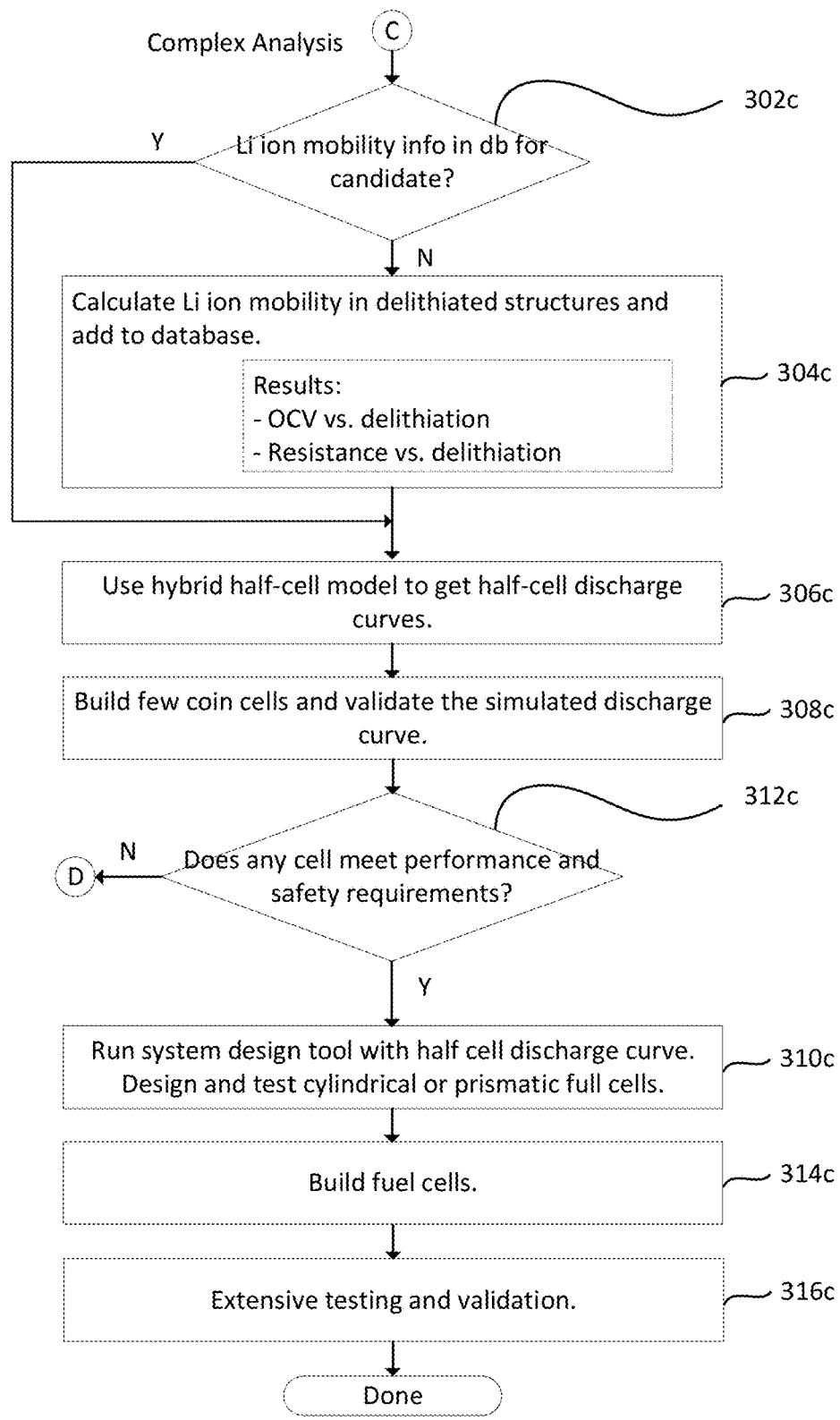
Figure 3D:
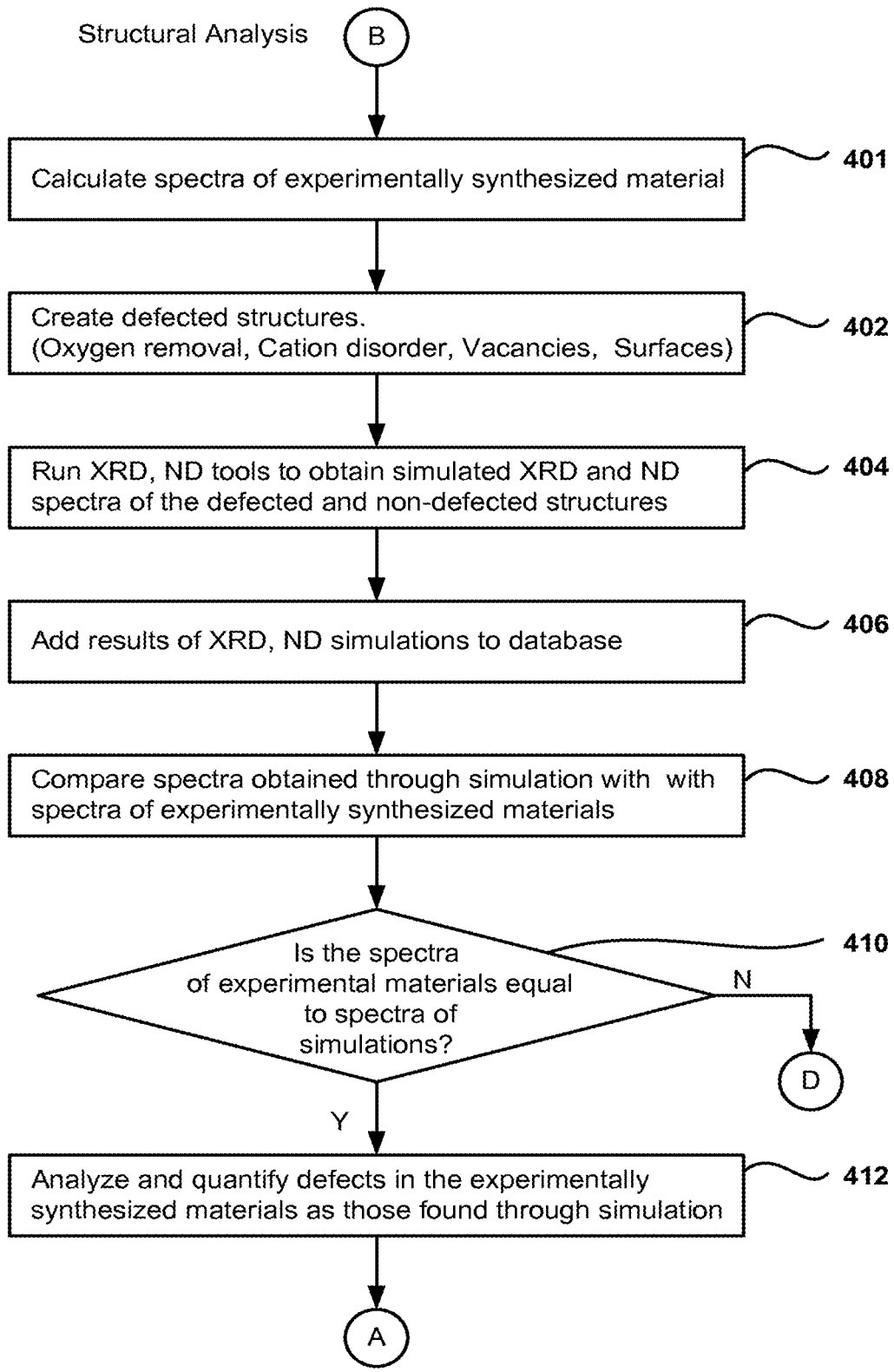
Figure 3E:
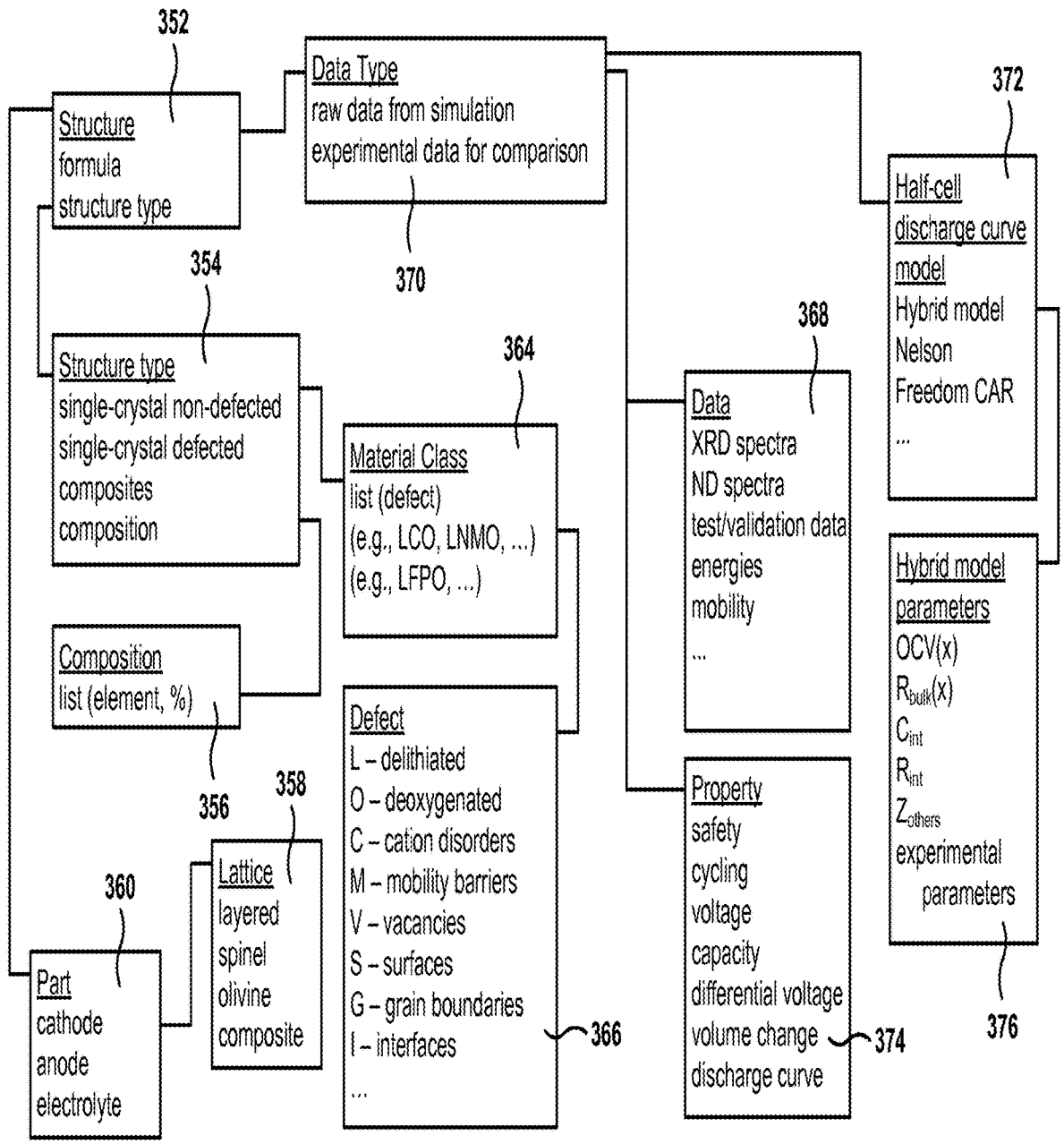
FIG. 3E illustrates a same structure of the database holding battery material information, according to one embodiment.

FIG. 3E illustrates a sample organization of the database holding battery material information, according to one embodiment. Field 352 defines the structure for which different types of data are kept, such as the data defined by fields 368, 370, and 374, described in more detail below. Structure 352 is defined by a formula and a structure type, which is defined in field 354. The structure type 354 can be single-crystal non-defected, single-crystal defected, composites (mixture of two or more single types), or a compositional formula representing the structure. The compositional formula is defined in field 356, which includes a list of different elements, such as Ni, Co, Mn, etc. Each element is included in the formula with a given percentage to form the compositional formula.

Structure type 354 is associated with a material class 364, which includes a list of defects in the structure. Examples of the material class include Lithium Cobalt Oxide (LCO), Lithium Nickel Manganese Oxide (LNMO), Lithium Iron Phosphate Oxide (LFPO), etc. The different types of defects are defined in field 366, and include delithiated (L), deoxygenated (O), cation disorders (C), mobility barriers (M), vacancies (V), surfaces (S), grain boundaries (G), interfaces (I), etc. Part 360 defines whether the structure is being used as a cathode, an anode, or an electrolyte. Further, field 358 defines the lattice for the cathode, such as layered, spinel, olivine, or composite.

Field 370 defines whether the data type corresponds to raw data from simulation or the data is experimental data for comparison. In other embodiments, other types of data are also kept in the database, such as test data, experimental data, etc. Some simulation data is kept in records associated with field 368, which includes spectra obtained through XRD or ND simulations, test and validation data, energies of the structures, mobility, etc. Field 374 includes values for one or more properties of the structure, such as safety, cycling, voltage, capacity, differential voltage, volume change, discharge curve, etc.

Field 372 defines the algorithm used for the simulation, that is, the half cell discharge curve model such as the hybrid model described herein, Nelson model, the FreedomCAR model, etc. Each of the models may store some of the calculations or parameters obtained during the simulation. For example, field 376 keeps the values obtained when using the hybrid model. The hybrid-model values include Open Circuit Voltage OCV(x), $R_{bulk}(x)$, $C_{int}$, $R_{int}$, $Z_{others}$, experimental parameters, etc.

It should be noted that some of the fields or records described above may be empty for some structures, as not all data is required or obtained at the same time. For example, the test/validation data is only calculated when requested by the user or by a computer program. It should be also noted that the embodiment illustrated in FIG. 3E is exemplary. Other embodiments of the database may utilize different arrangement of the data or different fields. The embodiment illustrated in FIG. 3E should therefore not be interpreted to be exclusive or limiting, but rather exemplary or illustrative.

Returning to FIG. 3A, in operation 304a user inputs are captured. In one embodiment, the inputs include the material class or type, the composition, and the formula, but other inputs, such as morphology, particle size, etc., are also possible. The inputs can be obtained using the GUI described below with reference to FIG. 11. Next in operation 306a, the method selects suitable building blocks from the database and combines the selected blocks to create all possible models of complex structures. Additionally, the system generates the relative total energies for all the possible models of complex structures.

In operation 308a, the models of the structures are grouped by the corresponding relative total energies in order to screen for stability. The method constructs a composite model set of derivative or daughter structures containing two or more transition metal atoms by calculating a linear average of parent components from the building block database of hypothetical structures to determine the lattice constants and atomic coordinates of candidate composition models. The structures obtained this way are found to be nearby a total energy minimum.

Next, in operation 310a the method screens or classifies the composite model set by employing a local order matrix to sub-classify each composite model into a subset or group such that the composite models in each subset or group share the similar property in local transition metal ordering. A representative model from each subset or group is then selected according to its stability. The selected candidates from each subset or group are ranked in terms of the relative total energies or the highest stability criteria. The most likely candidates are chosen according to their ranks, i.e., according to their lowest total energy or highest stability criteria.

FIG. 3D describes a method for performing structural analysis of the candidate materials. FIGS. 4A-4B and 5A-5B, described in more detail below, present structures and results obtained during the structural analysis. The data related to experimentally obtained materials is kept in the database. However, the actual composition of these experimentally obtained materials is not known. One embodiment of the invention is used to compare the data obtained through simulation with the data from experimentally obtained materials. Once a match is found, the method then determines the composition of the experimentally obtained materials as that of the corresponding simulated structures with the same spectra. The structural analysis is based on XRD of quantum simulated and screened structures according to their stability, as previously described with reference to operations 108 and 110 to quantify the structurally defected and modified materials structures.

In operation 401, the spectra of an experimentally synthesized material is obtained and then stored in the database. In operation 402 the defected structures are selected based on the properties to be analyzed (e.g., oxygen removal, cation disorder, vacancies, surfaces, etc.) In one embodiment, the same structures selected in operation 110 of FIG. 3A are chosen. In other embodiments, a subset of these defected structures is chosen. Any ratio, fractional amount, and compositional mixtures of the cation disorder, vacancy creation, surfaces, oxygen removal type point defects as well as phase and grain boundaries type crystal structure defects can be calculated in the simulated materials structures.

Figure 4A:
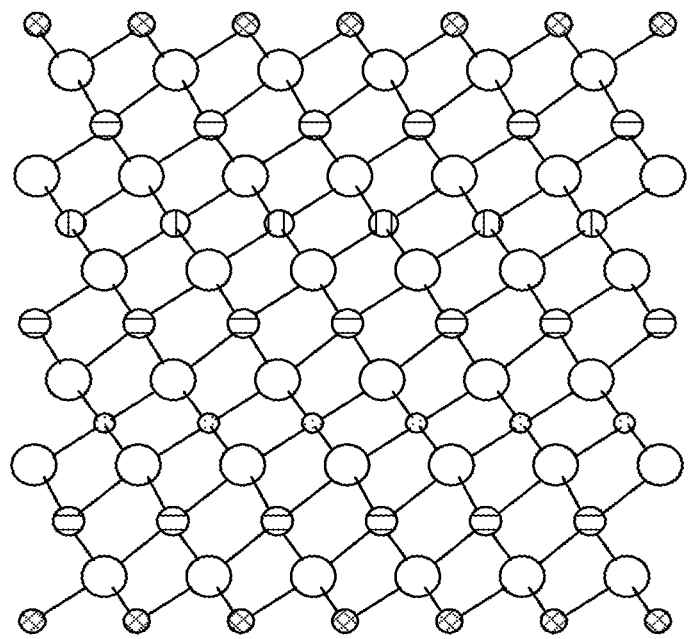
FIGS. 4A and 4B illustrate the crystalline structures of an ideal and a cation disordered defected lattice structures, according to one embodiment.
Figure 4B:
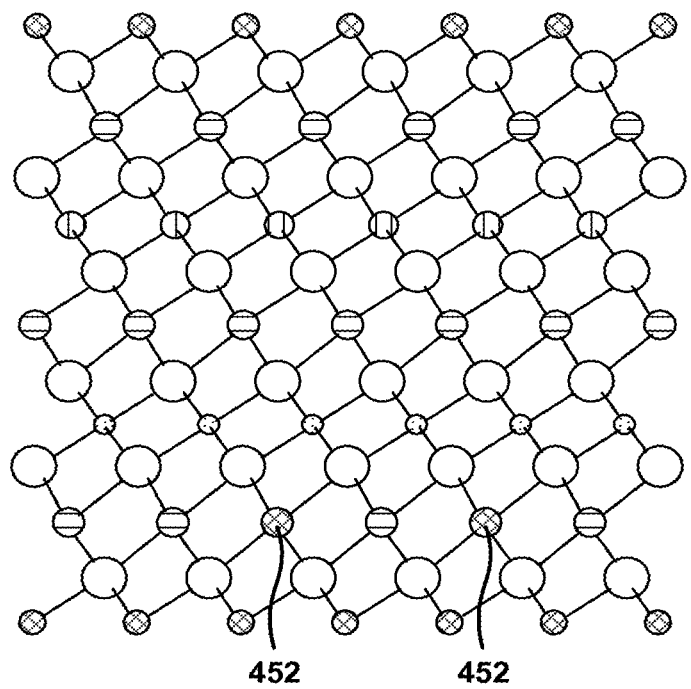

The user can select a type of defect (e.g. oxygen removal) using the GUI in the development engine, and then the user or the development engine creates different defected structures for that type of defect by changing the amount of defect introduced (10%, 15%, 20%, etc.). For example, the crystalline structures of the ideal $LiNi_{1/3}Co_{1/3}Mni_{1/3}O_2$ is shown in FIG. 4A, and the crystalline structures of the cation disordered defected $LiNi_{1/3}Co_{1/3}Mni_{1/3}O_2$ is shown in FIG. 4B, where 11% of the Li is exchanged with Ni in $LiNi_{1/3}Co_{1/3}Mni_{1/3}O_2$. The transition metal atoms layer (third row from the bottom in FIG. 4B) shows the exchange of Li with the transition metal atoms 452 in the layer.

As previously discussed, the quantum simulated relaxed and defected structures of battery materials are generated with the development engine. The coordinates of these structures are used as inputs for the integrated XRD/ND simulation tool which returns in operation 404 the simulated XRD/ND spectra of QS simulated pristine and defected materials structures. The resulting spectra for the pristine and the defected structures are described in more detail below with reference to FIGS. 5A and 5B. The results of the XRD and ND simulations are added to the development engine database in operation 406.

The suitable geometry and the suitable stoichiometry compositions of the ideal and defected materials structures are obtained in order to design the new battery materials, as well as quantifying the defects in the generated materials. In one example, the simulation produces a defected structure of the cation disorder by exchanging the coordinates of one pair of the Ni—Li atoms in the structure, and then producing the XRD structure.

The results from experimentally synthesized materials are also included in the database. These synthesized materials are created in the lab by changing the synthesis conditions, such as temperature, duration of the experiment, impurities, etc. However, the composition of these experimentally synthesized materials is not exactly known due to the changes in the environmental conditions.

Returning to FIG. 3D, in operation 408 the simulated XRD patterns of the defected structures are compared to the XRD patterns of the experimentally synthesized materials. In one embodiment, the coordinates of the peaks in the spectra of the simulated structures are compared with the coordinates of the peaks from the experimentally synthesized materials. It should be noted that a certain margin of differences may be within normal tolerance, and a match may be determined when the spectra are substantially similar. In operation 410, the results of the comparison in operation 408 are used to determine whether the method flows to connector D (i.e., back to the beginning to restart the process) when no match is made, or flows to operation 412 when a match is made. In operation 412, the amount of the defects in the experimentally synthesized materials is then determined as the defects in the corresponding simulated structure. This allows the user of the development engine to identify and characterize defects in the defected compositions of the materials synthesized in experiments.

Figure 5A:
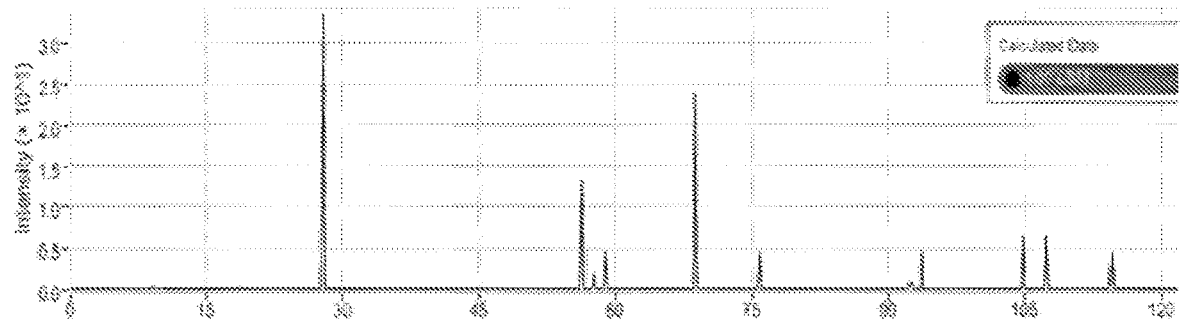
FIGS. 5A and 5B show the simulated XRD spectra generated by the development engine for the structures of FIGS. 4A and 4B, respectively, according to one embodiment.
Figure 5B:
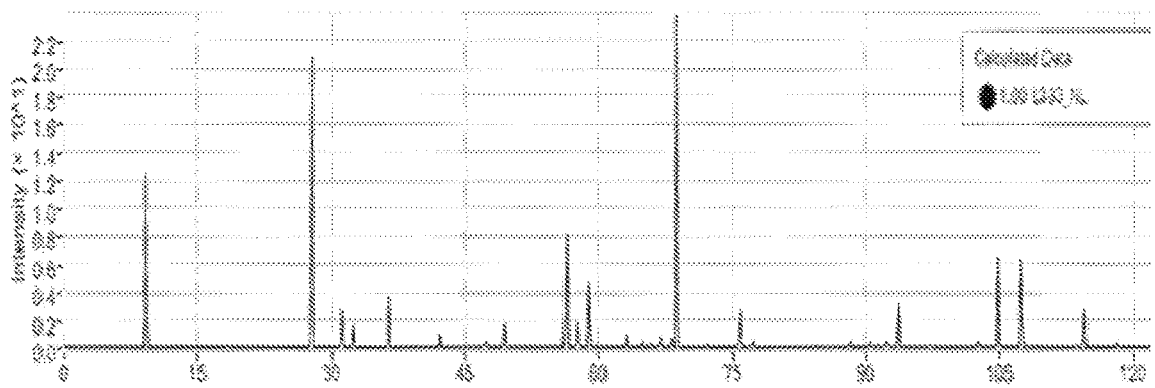

FIGS. 5A and 5B show the simulated XRD spectra generated by the development engine for the structures of FIGS. 4A and 4B, respectively, according to one embodiment. The comparison of the position and strength of the extra peaks in the XRD spectra of the defected structures in FIG. 5A with that of the pristine structures in FIG. 5B is used to characterize and quantify the defects in the experimentally synthesized materials. This is just one example of how to characterize cation defects in the experimentally synthesized materials structures using the simulated XRD spectra of the development engine. All other type of defects, such as those listed in field 366 of FIG. 3E, can also be similarly characterized by the simulated spectra created by the development engine and by comparing with the experimentally synthesized materials under different synthesis conditions.

Returning to FIG. 3B, in operation 302b the user selects which analysis to perform next, either a structural analysis or a battery property analysis. If the structural analysis is chosen, the method flows to operation 402 in FIG. 3D to perform the structural analysis, as previously described. If the user selects the battery property analysis, the method flows to operation 304b, as described above in operation 310a of FIG. 3A, where the most likely group of candidate structures is selected by the screening procedure. The method employed for battery property analysis is referred to herein as the battery Capacity and Voltage Prediction using Quantum simulations (CVPQ) method, which includes operations 304b, 306b, 308b, and 310b from FIG. 3B.

In operation 306b, the development engine determines which candidates are missing in the database of simulated structures and need a simulation. In operation 308b, new simulations are performed for the candidates, if any, that need a simulation, such as additional simulations for new building block structures. The results of the additional simulations are the delithiated structures and the energies of these delithiated structures. After operation 308b, the method flows to, operation 310b to run the fast material level analysis and obtain the value of the different parameters, such as voltage, volume change on charging/discharging, capacity, relative safety, relative cycling, etc.

The first operation in the fast material level analysis includes performing standard Quantum Mechanical (QM) total energy calculations at different delithiated structures. A sample calculation for $Li_xCoO_2$ (LCO) is included below for illustrating purposes, such that the CVPQ method calculates standard QM total energy calculations at different delithiated structures for the variable x in $Li_xCoO_2$. Delithiated structures of $Li_xCoO2$ are derived structures from a fully lithiated LCO structure. However, the symmetry of $Li_xCoO_2$ is not necessarily the same as that of fully lithiated LCO. In one embodiment, delithiated structures are constructed from fully lithiated LCO that can be made by using modeling methods, such as the one illustrated in FIG. 3A. For example, a minimum of three or more sampling points 20 of lithium concentration are selected for evaluating the electrochemical characteristics, such as working voltage and capacity.

The QM total energy calculations can be performed by all available first-principle approaches, such as DFT-based methods, all of its variants, and all of its equivalents known by different names, as well all the semi-empirical methods where some parts of the total energy function are approximated and some parts are simulated. The averaging of the simulated electrochemical characteristics, such as working voltage and capacity along the charge or discharge curves, is typically done over many simulated values of these characteristics, where each simulated value uses a minimum of three sampling points for different values of the variable x (delithiation.) The selection of a minimum of three sampling points for the value of x is exemplary and other embodiments of the method can use a different number of sampling points for different lithium concentrations. The larger the number of sampling points used in the procedure, the more accurate and reliable the finally predicted results will be.

The calculation of the average voltage for two lithium concentrations is performed using the following formula known in the art:

$$V(x) = \frac{-\{E[Li_{x_2}\ Host] - E[Li_{x_1}\ Host] - [\![(x]\!]_2 - x_1)E[Li]\}}{[\![(x]\!]_2 - x_1)}$$

In equation (1), E represents the total energy of the composite or solid solution and $X_1$ and $x_2$ are the lithium concentration sampling of the composites. It is preferable that the total energies used in equation (1) be calculated by the same QM method to avoid any inconsistency among different implementations of QM. Additionally, it is preferable to use the same approximation for all energy functional terms to avoid any inconsistency among different energy functional approximations. For example, one DFT package may implement several Generalized Gradient Approximations (GGA) versions, such as GGA+U or screened exchange (SX). In this case, if data from different implementations of the DFT on different parent building blocks has to be used, then proper scaling methods are used to bring the data to a same relative reference value before using the data in the above procedure. It is also possible to combine data obtained from different methods using proper scaling procedures, although the thus obtained results will typically be less accurate.

The fast evaluation method approximates the electrochemical characteristics of a candidate electrode as a cathode or as an anode in Li-ion Batteries (LIB) as a fitting function of lithium concentration (x), also referred to as a functional form of (x). Initially V(x) is calculated according to the following formula:

$$V(x) = V_{oc} + C_1(x-1) \quad (2)$$

In equation (2), the coefficients $V_{oc}$ and $C_1$ are fitting parameters derived from average voltages obtained from applying equation (1) using the total energies of the delithiated structures at different sampling points. The calculated values for LCO are presented in Table A below. Often, QM underestimates the voltage as compared to experimentally obtained voltage values. Therefore, in one embodiment, a phenomenal additional reference value correction is added to the parameter $V_{oc}$ depending on which property is to be corrected. This adjusted value of $V_{oc}$ is referred to as shifted $V_{oc}$. In another embodiment, the additional reference value correction for the same electrochemical property is kept the same for all the building blocks and simulated structures among the same family of the materials type. This way the relative values of the simulated electrochemical properties within the same material class or type are not affected. For example, an additional reference value correction of 0.6V can be used for the simulated capacity and 1.5V for the simulated nominal voltage in all LCO and layered-oxide type electrode materials irrespective of single or multiple transition elements used in the formulation. For different materials structure types, such as spinel or olivine, the additional reference value corrections are different and need to be accounted for when comparing the simulated values across different materials type.

The linear functional form in equation (2) is just one example of a linear functional form. Other formulas are also possible. For example, the linear case is one instance of a more generic fitting curve with the following definition:

$$V(x) = V_{oc} + C_1(x-1) + D(x-1)^2 + E(x-1)^3 \quad (3)$$

As in equation (2), in equation (3) $V_{oc}$ is related to voltage and $C_1$ is a parameter related to a capacity value. Further, D and E are parameters accounting for higher derivatives of the capacity.

Capacity is a function of the lithium concentration for a given working voltage window. The coefficients $V_{oc}$ and $C_1$ are determined by solving the fitting function (i.e., equation (2)) for two different values of x, as described above. The capacity of the material depends on the value of x at which $V(x)$ in equation (2) is equal to the cut-off voltage $V_{cut-off}$ for the cell. For example, the capacity of an electrode with cut-off voltage at 4.3V is different and less than the capacity of an electrode with cut-off at 4.6V. Which cut-off voltage is used (e.g., 4.3V or 4.6V) depends on the application under consideration. Therefore, once the cut-off voltage is fixed from the application view point, fitting function (2) is solved to find the x at which $V(x) = V_{cut-off}$. Once the value of x corresponding to the $V_{cut-off}$ is known, the capacity is calculated from the maximum capacity $Q_{mx}$ of the material. The capacity is equal to $xQ_{mx}$. The theoretical maximum capacity for any material is calculated by the chemical formula of the material. For LCO, $Q_{mx}$ is 274 mAh/g. Table A below, which is a summary of the results obtained using equation (2) shows that the QM capacity of LCO is 175 mAh/g at 4.3V cut-off. This value is similar to the charging capacity of 174 mAh/g and the discharging capacity of 171 mAh/g at 0.2 C at cut-off 4.3 V for coin cells data. This approach for the fast estimation of the capacity from the voltage profile emphasizes the low rate flat linear region of the voltage profile and assumes that the contribution at the edges near the lower and upper cut-off voltages are minimal and can be ignored for fast relative comparisons.

The nominal voltage of a cell is the average voltage over the discharging period, and is a function of the voltage cut-off. The nominal voltage in experiments is generally determined by the flat linear region of the voltage profile as a function of the state of charge. In the fast evaluation method, the nominal voltage is defined as an average between the $V_{cut}$ and the shifted $V_{oc}$ where $V_{cut}$ is the cut-off voltage as fixed by the application under consideration. The accuracy of the nominal voltage thus obtained can be iteratively increased by using more sampled data points for different lithium concentrations on the voltage profile, and by using an average value of the shifted $V_{oc}$ instead of the single value of the shifted $V_{oc}$ determined by only two lithium concentration data points. Further iterations using more sampled data-points of lithium concentrations along the voltage profile increase the accuracy of the predicted nominal voltage by the fast estimation method. For LCO, a QM nominal voltage of 4.1V is predicted, which is similar to the plateau between 3.9V and 4.2V observed in half cells using LCO as the cathode.

Table A below summarizes the results of applying the method for the sample Li concentrations of 1/2, 2/3, and 3/4.

TABLE A

| QM electrochemical calculations of LCO | | | |
|---|---|---|---|
| | Li Concentration x | | |
| | 1/2 | 2/3 | 3/4 |
| QM total energy (au) | −1547.7627 | −1549.0363 | −1549.6723 |
| Average voltage (V) (1/2, 2/3) | | 3.252 | |
| Average voltage (V) (2/3, 3/4) | | 3.000 | |
| Fitting coefficients | $V_{oc}$ −2.412 (V), Ci = −2.016 | | |
| Phenomenal corrections | Capacity shift = 0.6 V, Nominal voltage shift = 1.5 V | | |
| QM capacity | 175 mAh/g at 4.3 V vs. Exp charge/discharge capacity of 174/171 mAh/g | | |
| QM nominal voltage | 4.1 V vs. Exp plateau range: 3.9-4.2 V | | |

For composites that can be constructed using building blocks, the same CVPQ method illustrated above for the LCO example can be used to perform a fast evaluation of the electrochemical characteristics by treating the composite as a combined building block. For example, in the case of composite $Li(Ni_{1/3}Co_{1/3}Mn_{1/3})O_2$ (L333) the QM total energy calculations can be performed on three sampling points at different lithium concentrations and then follow the CVPQ method described above to derive the electrochemical characteristics.

Another embodiment for a method to perform fast evaluation of electrochemical characteristics of composite structures is described below. To illustrate the method, composite L333 is evaluated using individual building blocks' electrochemical characteristics previously obtained using the CVPQ method.

Table B below shows the electrochemical characteristics of individual building blocks Lithium-nickel oxide (LNO), LCO, and Lithium Manganese Oxide (LMO), which were obtained performing the CVPQ method illustrated for LCO.

TABLE B

| QM electrochemical CVPQ calculations of L333 from building blocks | | |
|---|---|---|
| Materials (cut-off at 4.3 V) | QM capacity (mAh/g) | Exp. Charging/discharging Capacity (mAh/g) |
| LNO | 213 | ~219 |
| LCO | 175 | 174/171 (0.2 C) |
| LMO | 210 | Unknown |
| L333 (bare) | 202 | 200/180 (1 C) |
| L333 (weighted) | 197 | |

A first strategy, referred to herein as strategy A, approximates the electrochemical properties of the composite structure using a Halpin-Tsai combination of the electrochemical properties of individual building blocks. As an illustrating example, the capacity of L333 is a special case of the following general formula:

$$Q(Lxyz) = f[x,y,z; Q_{LNO}, Q_{LCO}, Q_{LMO}] \quad (4)$$

In equation (4), the parameter f is a Halpin-Tsai type function with variables x, y, and z for the component ratio of each building block in a general composite Lxyz. In the case of L333, x, y, and z are all equal to 1/3. The fifth row of Table B shows the QM capacity of L333 to be 202 mAh/g by using the Halpin-Tsai type combination, as is known in the art.

A second strategy, referred to herein as strategy B, adopts a weighted Halpin-Tsai type combination according to the prospected different roles of individual building blocks in the composite phase. In strategy B, weighted Halpin-Tsai variables, such as $x*W_x$ are used instead of the bare Halpin-Tsai variables of strategy A. For example, it is assumed that LNO is the main capacity contributor because the valence of Ni ion goes from 2+ to 4+ during the discharging period. Other terms can be ignored. The sixth row of Table B shows the QM capacity of L333 to be 197 mAh/g when using the weighted Halpin-Tsai type combination (strategy B).

Both QM capacities obtained using strategies A and B are similar to the actual charging capacity of about 200 mAh/g and the discharging capacity at 180 mAh/g at 1 C. Columns 2 and 3 of Table B present the available simulation data and the experimental values. By comparing the values from columns 2 and 3, it can be observed that the fast method calculations obtained with the present method are similar for both individual building blocks and for composites.

Continuing with reference to FIG. 3B, after operation 310b, the method flows to operation 314b where a check is performed to determine whether any of the designed materials meet the basic requirements for the battery. If the result of the check is negative, then the method flows back to operation 304b in FIG. 3A. Otherwise, if the result of the check is positive, the method flows to operation 316b where a subset of the candidate materials is selected for complex analysis included in the simulation of half cell discharge curves. In another embodiment, all the materials that meet the requirements are selected. After operation 316b, the method flows to operation 302c of FIG. 3C.

With reference to FIG. 3C, operation 302c checks whether the Li ion mobility or diffusion data is present in the database for the candidate being analyzed. If the mobility or diffusion data is in the database, then the method proceeds to operation 306c. Otherwise, the method proceeds to operation 304c where the Li ion mobility in many delithiated structures is calculated. The final results of the additional calculations include the OCV and the resistance of the delithiated structures using the mobility or diffusion data. Once the Li ion mobility is calculated, the new results are added to the database.

In operation 306c, a hybrid half cell model is used to obtain the half cell discharge curves. The hybrid model is described below with reference to FIG. 6A. In operation 308c, coin cells are built to validate the simulated discharge curve of operation 306c.

From operation 308c, the method flows to operation 312c to determine whether there is any cell that meets the performance and safety requirements. If no cell meets the requirements, then the method returns to operation 304c to re-start the process. However, if one or more cells meet the requirements, then the method continues to operation 310c where cylindrical and prismatic full cells are designed with simulated half cell discharge curves. The thus designed and optimized prismatic and cylindrical full cells are then fabricated in operation 314c and tested in operation 316c for performance, safety, and cycling to validate the simulation results and choose the designed candidate material.

FIG. 6A illustrates the hybrid model for a typical half cell setup that consists of a cathode, an electrolyte separator, and an anode, according to one embodiment. The model is referred to as a hybrid model because it combines simulation data and experimental data. The data for the cathode or the quantum designed electrode is obtained using QM simulations and the data for the anode and the electrolyte is obtained via a few benchmark experiments for a given class of materials. The cell equivalent circuit is divided into a cathode equivalent circuit and a remainder equivalent circuit, which includes the electrolyte separator equivalent circuit and the anode equivalent circuit.

In other embodiments, the same methodology described herein is used for the anode and the electrolyte and the use of the hybrid model is not required. This means that the data for the anode and the electrolytes is calculated using simulations and stored in the database for use with the algorithms described herein to obtain data for the use of the different materials in building battery cells.

In accordance with the hybrid model, the electrolyte separator, which is soaked with appropriate electrolyte, allows Li ions to shuttle between two electrodes while electrically, isolating the two electrodes. In one embodiment of a half cell, the anode is a Li metal. The electrochemical characteristics of a half cell are mainly determined by the electrochemical properties of the cathode or designed materials. The hybrid model includes, (1) creating an equivalent circuit of the cell, and (2) determining the values of the components in the equivalent circuit.

The circuit components of FIG. 6A are grouped into three distinct groups according to their relations to the lithium concentration x in the cathode. The first group is the Open Circuit Voltage OCV(x) and bulk resistor $R_{bulk}(X)$. Both OCV(x) and $R_{bulk}$ are highly dependent on the lithium concentration of the cathode. The second group is a pair of components connected in parallel, an interface capacitor and an interface resistor, $C_{int}$ and $R_{int}$. This pair of components addresses the electrical contribution by the cathode and the electrolyte interface. A simple approximation to the cathode-electrolyte interface includes the parameters $C_{int}$ and $R_{int}$ used to represent a weak dependence on the lithium concentration of the cathode.

The third group corresponds to the Li metal anode and is parameterized into a single impendence $Z_{others}$. It is assumed that $Z_{others}$ is independent of the lithium concentration of the cathode. Therefore, $Z_{others}$ contributes universal electrical impedance to the electrochemical characteristics of a half cell. In one embodiment, the polarization effects on the metal-electrolyte interface are considered insignificant and a real resistor $R_{others}$ is used instead of the complex $Z_{others}$.

The hybrid model presented in FIG. 6A is one example of a circuit representation for the different components of a battery. Other embodiments of the invention may use other combinations of elements. For example, in one embodiment, the electrolyte separator includes more than one resistor connected in series or in parallel, and one or more capacitors connected in series or in parallel with any combination of the resistors for the equivalent circuit of the electrolyte separator. Similarly, the anode can be represented by several impedances connected in series, in parallel or in a combination of series and parallel connections, where each impedance can be a resistor or a capacitor.

In another embodiment, the anode parameters are obtained thorough simulation (as previously discussed for the cathode), and the cathode parameters are obtained through experimentation. Moreover, any combination of simulated data and experimental data for cathode, anode, and electrolyte can be used in different embodiments of the invention.

The accuracy of the hybrid model depends on how each circuit component is parameterized. In one embodiment, the parameterization combines partial experimental fitting with QM determination for certain components in order to retain a high degree of prediction power to LIB materials and system designs. The more QM determination is used for the individual circuit components, the more powerful the prediction and improvement of LIB materials and system designs. In one embodiment, QM calculations are performed to determine the bulk properties of the cathode, and then other components are fit for the properties of the benchmark half cell data for a given class of materials.

FIG. 6B summarizes the impact of the parameters of the equivalent circuit of FIG. 6A. In regard to the relationship to the cathode, the relationship to the cathode by the OCV(x) and $R_{bulk}(x)$ are the parameters in bulk material, the parameters $C_{int}$ and $R_{int}$ are related to the interface material, and $Z_{others}$ is not related to the cathode. Regarding the effect of the Li concentration x, OCV(x) and $R_{bulk}(x)$ have a strong relationship to the Li concentration in cathode, $C_{int}$ and $R_{int}$ have a moderate dependence on the Li concentration in cathode, while $Z_{others}$ is not dependent on the Li concentration in cathode.

FIG. 6C illustrates the accuracy level of predicted battery properties based on the amount of experimentation or simulations performed. As previously discussed, the accuracy of the results is related to the amount of simulations performed, but the accuracy is also related to the fact whether the data is collected via QM simulations or from actual experimentation. The least amount of accuracy corresponds to the data obtained only through simulation, while the most accurate data on the discharge curve is obviously obtained by experimentation, because accuracy is a measure of the difference between the simulated and experimentally measured discharge curves. In the middle of these two extreme approaches, the hybrid model combines QM simulation data with experimental data on a few benchmark materials in a given class to obtain the simulated discharge curves, which are faster to obtain and are accurate enough to filter or screen many candidate structures to make a short list before synthesizing the needed materials performing the actual electrochemical testing.

Figure 7C:
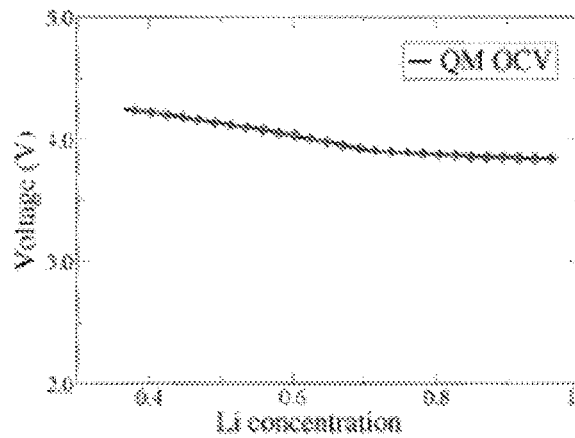
Figure 7C:
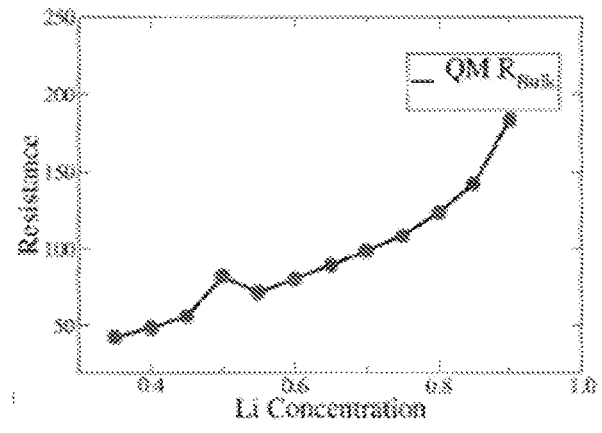
Figure 7C:
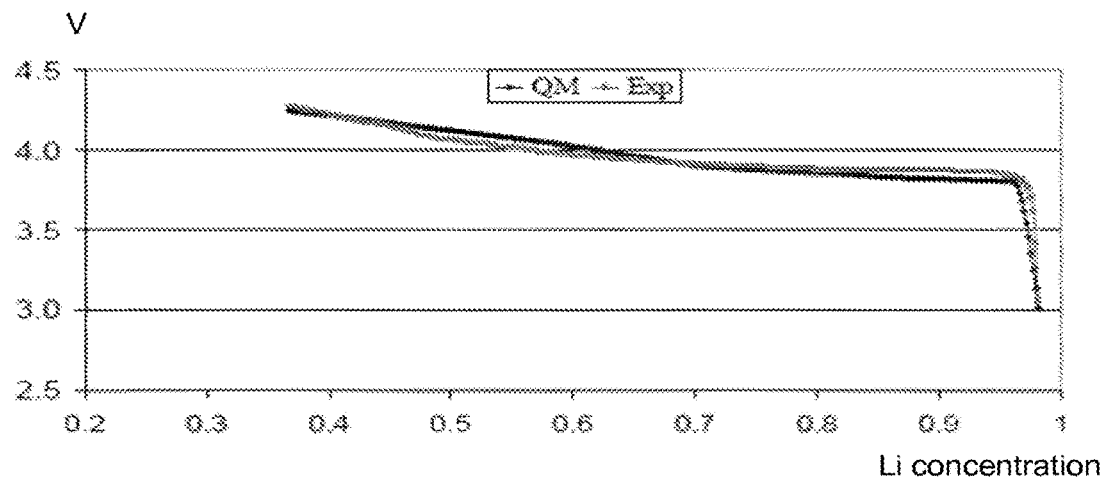

FIGS. 7A-7C illustrate the benchmarking of the hybrid model for a half cell of $LiCoC_2$ according to one embodiment. FIG. 7A illustrates the QM calculated OCV(x) for an LCO cathode at 0.2 C and for different Li concentrations. FIG. 7B illustrates the QM calculated $R_{bulk}(x)$ for the different Li concentrations. Further, FIG. 7C shows the fitted discharge curve and a comparison with experimental coin cell data. FIG. 7C shows that the fitted discharge curve is almost the same as the discharge curve measured through experimentation.

Figure 8:
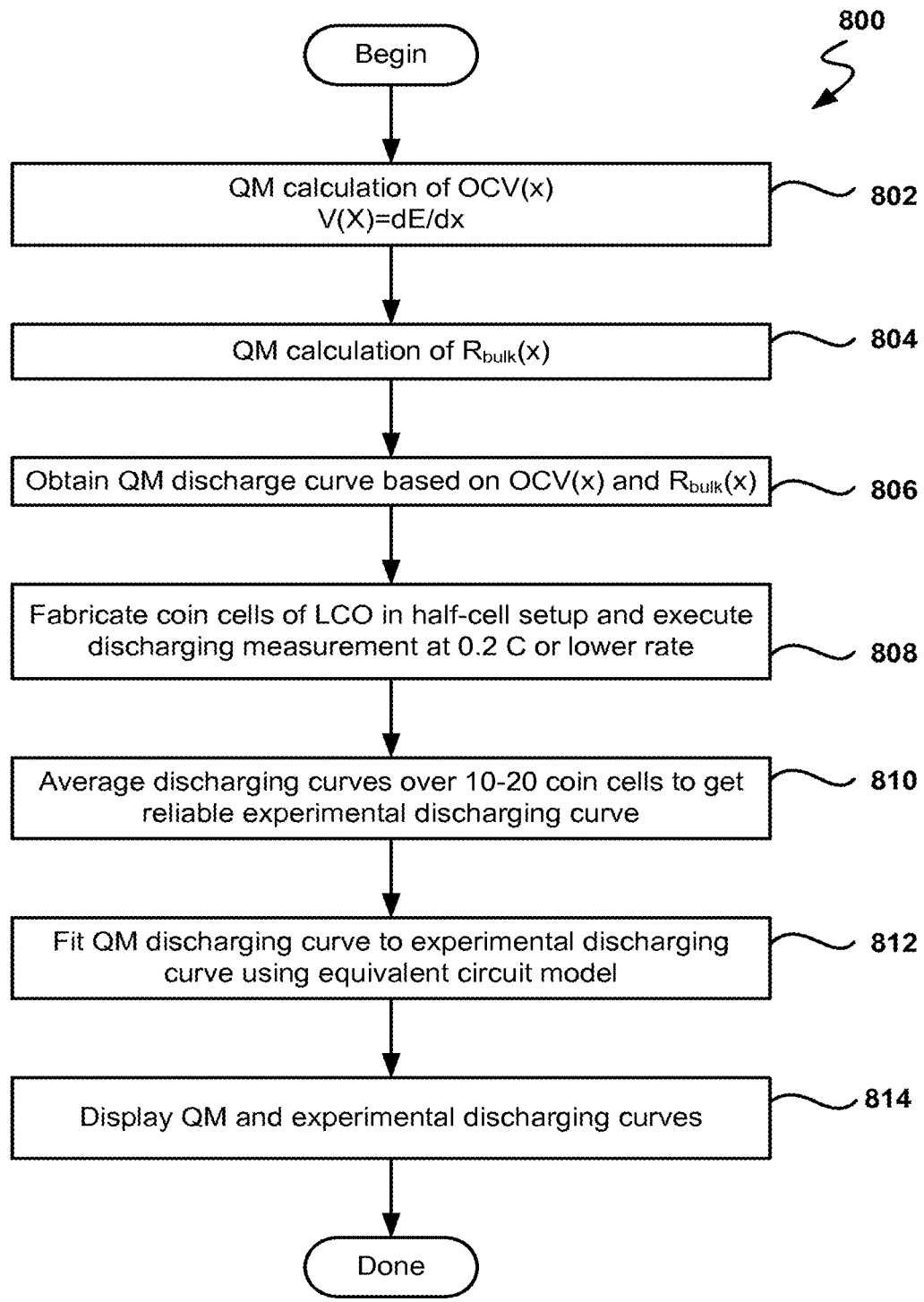
FIG. 8 shows a flow chart of a method used to calculate the simulated curves of FIGS. 7A-7C, in accordance with one embodiment.

FIG. 8 shows a flow chart of a method used to calculate the 20 simulated curves of FIGS. 7A-7C, in accordance with one embodiment. In operation 802, the method performs a standard QM calculation of OCV(x) using the following formula:

$$OCV(x) = -\{G[Li_{x2} \text{ Host}] - G[Li_{x1} \text{ Host}] - (x_2 - x_1)G[Li]\}/(x_2 - x_1) \quad (5)$$

In equation (5), G is the Gibbs free energy as a function of the delithiated structure [Lix Host], where $x_1$, $X_2$ are concentrations of the delithiated host lattice in the application range of interest of the composites. G[Li] corresponds to the Gibbs free energy of individual Lithiums. The more sample points and the more accurate QM, then the more accurate the OCV(x) will be.

In operation 804, a standard QM calculation of $R_{bulk}(x)$ is performed by executing ion diffusivity or mobility transition barrier calculations as is known in the art. See, for example, A Van der Yen, G. Ceder, Journal of Power Sources 97-98, (2001) 529. Further, in operation 806 the method combines the OCV(x) from operation 802 and the $R_{bulk}(x)$ from operation 804 to obtain the bulk QM discharging curve using the equivalent circuit model of FIG. 6A.

Standard coin cells are fabricated during operation 808 by using a LCO cathode in a half cell setup. Discharging measurements at 0.2 C or at other rates are then performed. In operation 810, the method averages the previously obtained discharging curves over at least 10-20 coin cell data points to get a reproducible and reliable experimental discharging curve.

In operation 812, the method fits the QM discharging curve to an experimentally parameterized discharging curve using the equivalent circuit model illustrated in FIG. 6A, including the anode and the electrolyte. The development engine displays the combined discharge curve as the total discharge curve of the coin cell or half cell made with the QM designed and parameterized cathode and the experimentally parameterized anode and electrolyte. As can be observed in FIG. 7C, the QM curve obtained approaches the experimental discharging curve fairly well. In one embodiment, the QM and experimental discharging curves of FIGS. 7A-7C are displayed by the development engine on a display during operation 814.

Another application of the hybrid model is the prediction of the electrochemical characteristics of new cathode materials, even when real synthesis and discharge curve data on the new material is not available. This is achieved by simulating QM prediction of the relative electrochemical discharge characteristics with respect to the benchmark material such as LCO for single-crystalline layer oxides. An example is presented below to illustrate this method for L333 (i.e., $LI(Ni_{1/3}Co_{1/3}Mn_{1/3})O_2$) type materials. The following operations are performed:

1. Perform a standard QM calculation of OCV(x) for L333 using the same QM method and the same lithium concentration sampling mesh (x), and calculate dOCV(x) as the OCV difference between L333 and LCO point by point, i.e., $dOCV(x) = OCV_{L333}(x) - OCV_{LCO}(x)$. As previously discussed, the more Li concentration points are sampled, the more reliable the QM calculation procedure will be.

2. Replace $OCV_{LCO}(X)$ with $OCV_{L333}(x)$, and perform the hybrid method illustrated in FIG. 8 for LCO to get a QM discharging curve for L33 at low rates 3. Perform standard QM calculation of $R_{bulk}(x)$ for L333 using the same QM method and the same lithium concentration sampling mesh (x), and calculate $R_{bulk}(x)$ difference $dR_{bulk}(x)$ between L333 and LCO point by point, $dR_{bulk}(x) = R_{bulk:L333}(x) - R_{bulk:LCO}(x)$. The more samples are calculated, the more reliable the QM calculations will be.

4a. Use $R_{bulk}(x)$ for L333 to replace $R_{bulk}(x)$ for LCO, and then perform the CVPQ method to get a QM discharging curve for L333 at low rates.

4b. In another embodiment, the method uses both $OCV_{L33}(x)$ from and $R_{bulk}(x)$ for L333 to replace the same term for LCO and then perform the CVPQ method to get a QM discharging curve for L333 at low rates.

Figure 9A:
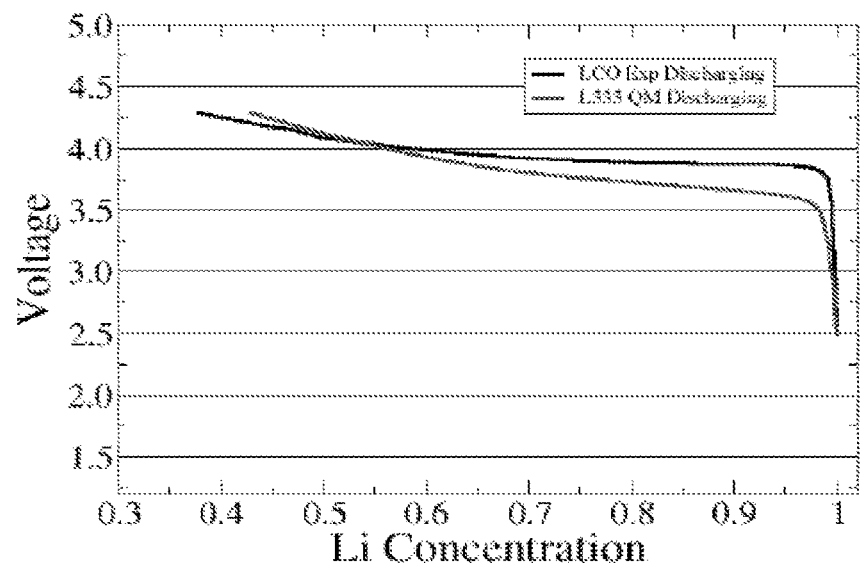
FIGS. 9A and 9B present the Quantum Mechanical (QM) discharging curve using the hybrid model as well as a comparison to a half cell data using L333 as the cathode, according to one embodiment.
Figure 9B:
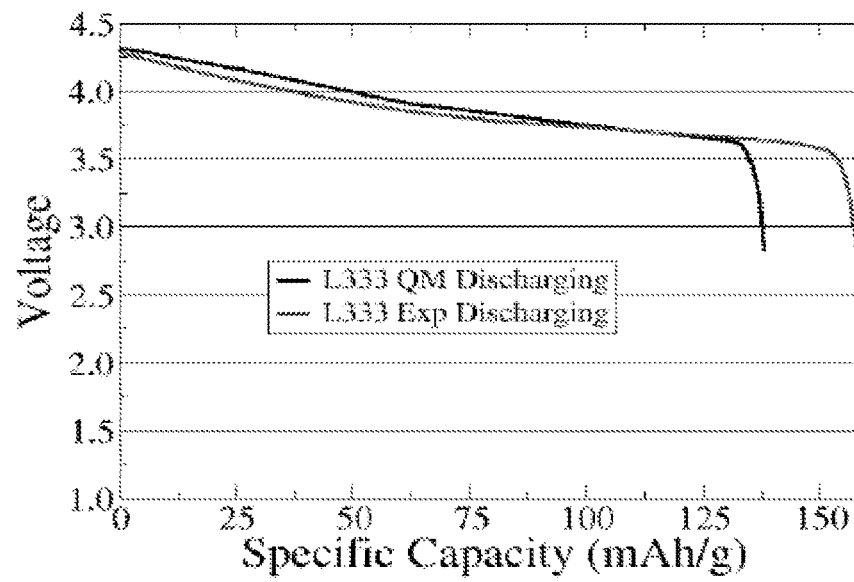

4c. In another embodiment, the previously obtained OCV 5 difference, dOCV(x), is added to the LCO coin cell discharging curve according to the equivalent circuit model of FIG. 6A. FIGS. 9A and 9B present the QM discharge curve using the hybrid model as well as a comparison to a half cell data using L333 as the cathode, according to one embodiment. The QM discharging curve fairly approximates the experimental coin cell data.

4d. In another embodiment, the calculated $R_{bulk}$ difference, $dR_{bulk}(x)$, is added to the LCO coin cell discharging curve according to the equivalent circuit model and then follow the method of operation 4c to derive a new QM discharging curve.

4e. Another embodiment uses both dOCV(x) and d $R_{bulk}$(x) and adds them to the LCO coin cell discharging curve according to the equivalent circuit model.

In general, the more QM calculations of OCV, $R_{bulk}$ and their differences with respect to LCO are performed, the more accurate and powerful the prediction of the discharging curves will be.

Figure 10A:
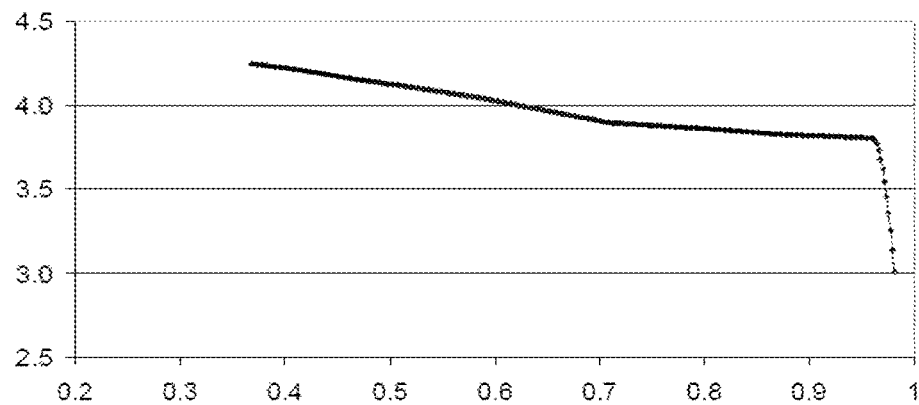
FIGS. 10A-10C illustrate an embodiment of a method for predicting the electrochemical characteristics of full cells with new cathode materials, even when real synthesis is not available, applying the hybrid model.
Figure 10B:
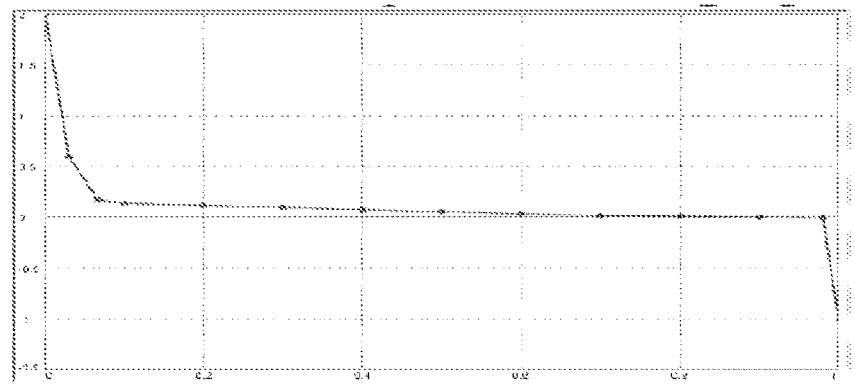
Figure 10C:
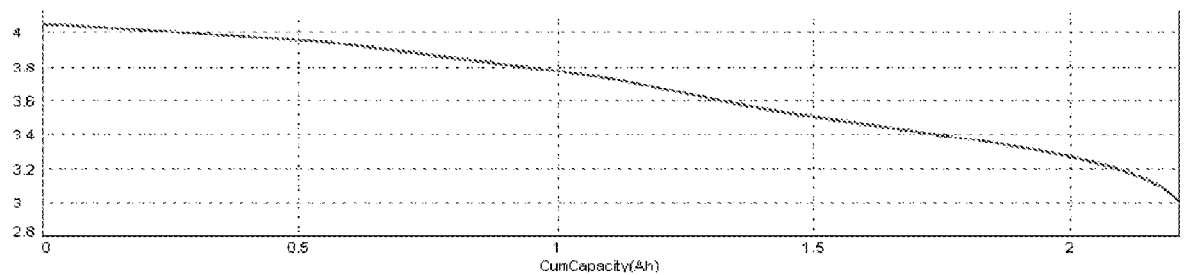

FIGS. 10A-10C are graphs that illustrate an embodiment of a method for predicting the electrochemical characteristics of full cells with the newly QM simulated or designed cathode materials, even when real synthesis is not available, by using the simulated discharge curves and the above-described hybrid half cell model. Full cells can be constructed from two half cells that have different voltage-capacity characteristics. The method is illustrated by constructing the discharge curve of a typical 18650 battery, which uses LCO as the cathode and graphite as the anode. In one embodiment, the same QM discharge curve of FIG. 10A is used from the example of LCO for cathode previously described with reference to FIGS. 7A-7C. In addition, the coin cell discharging curve of a graphite as the anode is also used, as shown in FIG. 10B. The full cell discharging curve is a combination of the two discharging curves according to the following equation;

$$V\text{full cell}(x) = V\text{cathode}(x) - V\text{graphite}(x) \qquad (6)$$

In another embodiment, the simulated half cell discharge curve data of the designed or developed cathode, using the hybrid model described above, is passed as an active cathode material input discharge curve to any full cylindrical or prismatic cell design, testing, and validation tool such as Battery Design Studio (BDS), which is a commercially available tool from Battery Design LLC, or any other such tool. The BDS uses the QM simulated discharge curve of the cathode, under the hybrid model, as the input active cathode material discharge curve. BDS allows choosing all the cathode side slurry parameters, such as particle size, surface area, Li concentration, binder type and concentration, and conducting agent type and concentration. BDS allows the design of the full cylindrical or prismatic cell positive electrode or cathode with QM simulated discharge curve using the hybrid half cell model. In another embodiment, BDS similarly allows choosing the anode and electrolyte from a database of standard anodes and electrolytes used in industry and academia.

In another embodiment, the QM designed and developed cathode or positive electrode material, using simulated half cell discharge curves with the hybrid model, can be combined with standard anodes or electrolytes available from the BDS database to design cylindrical or prismatic full cell batteries and simulate their electrochemical discharge and safety characteristics.

In yet another embodiment, the QM designed and developed cathode or positive electrode material, using simulated half cell discharge curves with the hybrid model, can be combined with customized anodes or electrolytes, for which data is available from any other source, or data that can be generated in experiments, to design cylindrical or prismatic full cell batteries to simulate their electrochemical discharge and safety characteristics.

In another embodiment, it is possible to test and validate the designed or developed positive electrode or cathode against standard or customized anodes or electrolytes. They are tested and validated for performance and safety characteristics at the system level for full cylindrical or prismatic cell configurations. The test and validation are performed on a computer to screen or short list the candidate materials before any materials synthesis is performed, and a full cell is designed and developed for the synthesized material.

The accuracy of the designed, tested and validated material at the system level full cylindrical or prismatic cells will depend on the amount of QM simulated positive electrode or cathode material data together with amount and accuracy of experimentally measured anode, electrolyte, or interface related data.

In another embodiment, it is possible to extend this methodology is extended to use QM simulated or new anode and electrolyte data with standard, designed or developed new cathode material data as well.

FIG. 10C shows an example of a discharge curve at 1 A current for a typical 18650 full cylindrical cell battery, which yields a capacity of 2.2 Ah, fairly matching the actual capacity of existing 18650 batteries. Similar discharge curves with typical prismatic cells are also feasible with the development engine methodology.

Figure 11:
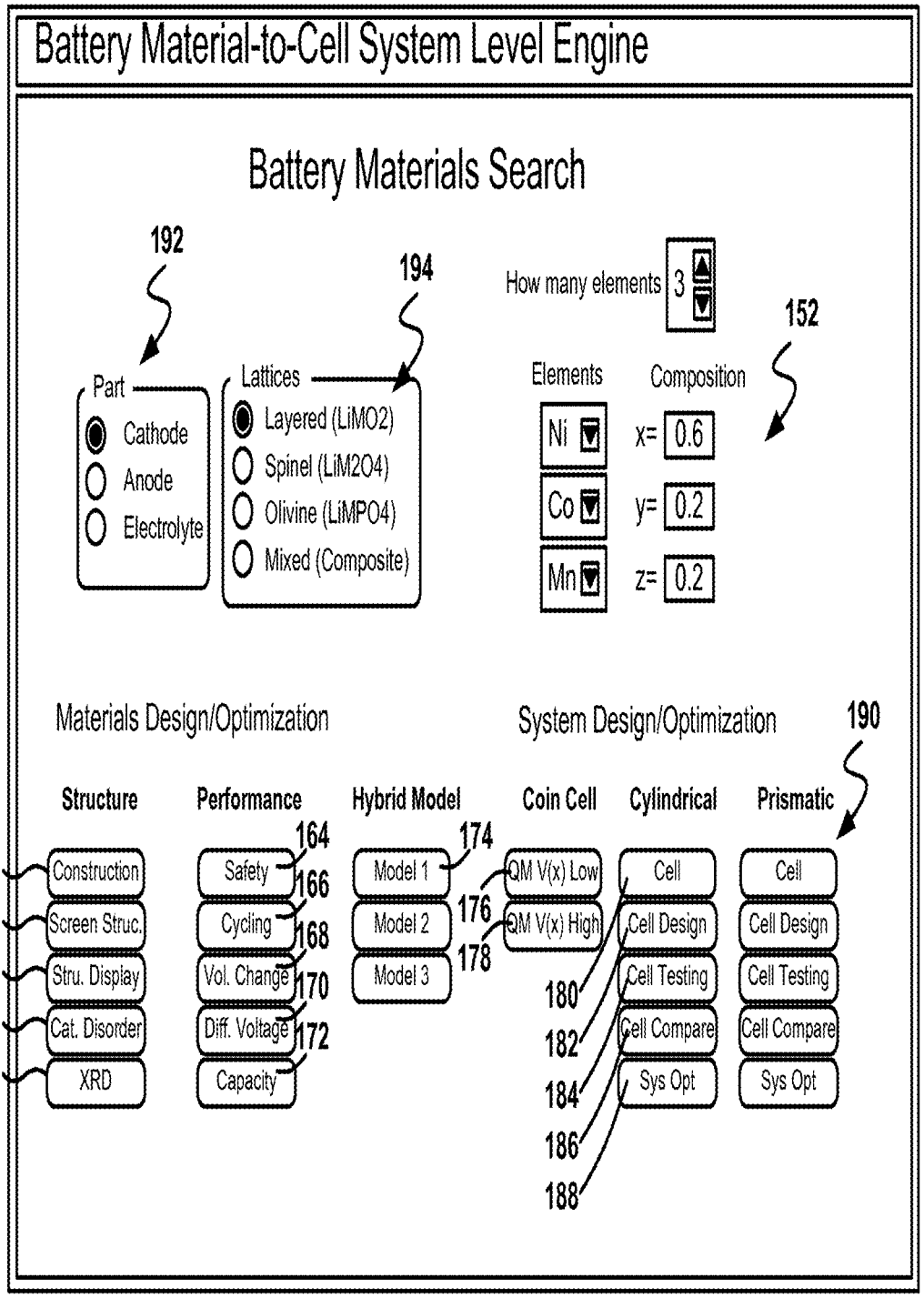
FIG. 11 illustrates one embodiment of a Graphical User Interface (GUI) of the development engine for searching battery materials.

FIG. 11 illustrates one embodiment of a Graphical User Interface (GUI) of the development engine for searching battery materials. The GUI sets up an interaction mechanism between a user and the computer program, including database data and logic flow, for the candidate electrode material's screening-optimization procedures. The search for materials includes the goals of obtaining better safety, cycling ability, nominal voltage, higher capacity, and increased power. It allows the selection of electrode materials and combinations of selected electrolyte materials for system level cylindrical or prismatic cell design.

The development engine is based on the database of QS-DFT simulated modular building block structures and implements one or more of the previously described physics-based hierarchical models. Further, the development engine implements the design and screening rules to search for new battery materials compositions enabling the user to interactively manage and organize the process flow to perform the following tasks:

(a) Receive user input to select the single, composite, or solid solution lattice types, mole or composition ratio of active elements, and end functional group to determine the composition to be screened;

(b) Create a set of all possible models of the target composition from the database of modular building blocks;

(c) Structurally screen the set of generated models to separate the models into groups that need to be simulated for the targeted structural, safety, and performance characteristics;

(d) Display the structural models and their X-ray diffraction spectra for comparison or validation with experimentally synthesized compositions;

(e) Simulate and display the relative safety, cycling ability, nominal voltage, capacity and volume change on charging/discharging characteristics of the selected composition to screen the structures by comparing them with a chosen benchmark or according to the user required criteria;

(f) Simulate and display the electrochemical discharge characteristics of the chosen or selected composition, using the hybrid model, in comparison with the discharge characteristics of the benchmark materials composition within the chosen class of material; and (g) The simulated discharge characteristics results obtained for the chosen or screened composition are combined with the user supplied input on morphology, surface area, and tap density to design cylindrical or prismatic electrodes and cells with the required safety and performance characteristics.

The development engine allows designers to rapidly eliminate non-performing compositions and focus their efforts on the promising candidates. The design process is guided by the development engine and can be broken into four phases that can be iterated until desired results are achieved. These four phases are:

Phase 1: Material Composition & Structural Analysis;
Phase 2: Material Intrinsic Electrochemical Properties;
Phase 3: Link to Coin Cell or Half Cell System Discharge Curves; and
Phase 4; System-level cylindrical or prismatic cell design, test, validation, and comparison performance.

It should be noted that the embodiments using four phases are exemplary. Other embodiments may utilize different number of phases and the operations in each phase may be different. The embodiments illustrated should therefore not be interpreted to be exclusive or limiting, but rather exemplary or illustrative.

In the embodiment shown in FIG. 11, the top half is dedicated for inputs and the bottom half includes buttons that perform calculations or present information on the display. After the user selects the inputs, such as the material composition, then the user selects which information is of interest. This way, the user gets information faster as the development engine does not need to compute all the possible items of information. If information is requested and is not available, the development engine calculates it on demand and informs the user that additional data is needed in the database to complete the desired task.

In phase 1, the elements and the composition are chosen. Radio buttons 192 allow the selection of the type of battery material: cathode, anode, or electrolyte. Additionally, the type of lattice can also be selected using radio buttons 194, including Layered, Spinel, Olivine, etc. Additionally, the number of elements, the elements, and the fractional composition for each element is selected in input area 152. For example, in the selection shown in FIG. 11, the formula $LiNi_xCoyMn_zO_2$ has been selected for 3 elements: Ni, Co, and Mn. The parameters x, y, z can be between 0 and 1 with x+y+z=1 (100%), and in the example shown x=0.6, y=0.2, and z=0.2, which means a composition of 60% Ni, and 20% each of Co and Mn.

When the user clicks button 154, the atomic scale models are constructed. For any chosen composition hundreds to thousands of atomic scale models are possible where Ni, Co, or Mn have distinct position assignments. The Construction button 154 causes the development engine to develop all possible models for structural and energy analysis for stability.

Screen structures button 156 is used to perform screening in the order of stability. For the chosen composition, all the generated models are screened and ordered in terms of relative energies and separated into groups, such that groups with lower energies are more feasible and structurally stable. Display and structural analysis button 158 causes the development engine to display, for the members of the selected groups, the analysis of atomic arrangements, bond, lengths, bond angles, etc.

Cation disorder button 160 is used for creating defects. Cation disorder defects in the created structures are responsible for performance degradation, which can be quantified with the use of XRD spectral analysis. The listing of cation disorder defect in button 160 is used as one example of the capability to examine and analyze different types of defects possible in the material. Other embodiments may utilize other types of defects such as oxygen removal or vacancy, vacancy creation, grain-boundaries, interfaces or surface defects. The option provided by button 160 should therefore not be interpreted to be exclusive or limiting, but rather exemplary or illustrative. The development engine creates the chosen percentage of defects, such as the cation disorders related to the cycling ability of the material. Clicking XRD button 162 starts the XRD/ND Analysis. The development engine allows fast and instantaneous analysis of X-ray and Neutron Diffraction spectra of the chosen composition and structures of the pristine and defected material. The resulting spectra are available for display. Both simulations can be compared with experimental data to characterize the experimentally synthesized material.

Phase 2 is categorized under the Performance section, and includes buttons 164, 166, 168, 170, and 172. Safety button 164 is selected to determine the relative oxygen release rate (ORR) in relation to safety. The intrinsic relative safety property of the chosen material is assessed by the relative ease with which oxygen is released by the material. The ORR is the transition rate computed by QM simulations of the activation energy of oxygen removal. The ORR is a pre-factor, which is determined by the ratio between the partition function at the transition location and the partition function of the initial configuration. When calculating the relative safety property of the battery, the relative ORRs are computed as a ratio with respect to the ORR of the benchmark material. Initially, for fast estimation, it can be assumed that the changes in the pre-factors are small with respect to the benchmark material as compared to the changes in the exponent factors arising out of the activation energies. However, ultimately as the database is populated over time with different transition states and with the corresponding pre-factors, the effect of pre-factors in the absolute ORRs could be included instead of the relative ORRs. The ORR, which can be shown on the display, is used in screening the chosen composition for safety. The larger the ORR, the less safe the chosen composition will be.

Cycling button 166 is labeled "Cycling" to calculate and display the intrinsic relative cycling ability at the material level by comparing the relative cation disorder formation rate. The intrinsic relative cycling property of the chosen material is computed by calculating the relative ease with which a Ni—Li, Co—Li, or Mn—Li exchange cation disorder is formed in the layered oxides and the formation of such defects is shown to reduce the intrinsic cycling-ability at the materials level. A relative cation disorder formation rate (CDFR) is used in screening the chosen composition for cycling ability. The CDFR is a transition rate computed by QM simulations of the activation energy of Ni—Li, Co—Li, or Mn—Li exchange and a pre-factor determined by the ratios of the partition function at the transition location to the partition function of the initial configuration before exchange. The relative CDFRs are computed as a ratio in respect to the CDFR of the benchmark material. For fast estimation, it can be assumed that the changes in the pre-factors are small with respect to the benchmark material when compared to the changes in the exponent factor 10 arising out of the activation of exchange energies. However, as the database is populated with different transition states and the pre-factors corresponding to those transition states, the effect of pre-factors in the absolute CDFRs can be included instead of the relative CDFRs. The larger the CDFR, the poorer the cycling ability of the chosen composition will be.

Button 168, labeled "Vol. Change," calculates and displays the volume change on charging and discharging. The charging and discharging of a battery cathode material involves removal and restoration of lithium ions. The difference between the volume of the initially relaxed structures and the volume of the same delithiated structures is the volume change computed using the QM methods. Further, the volume change of the material is computed as the percentage volume change as a function of the composition.

Button 170 calculates and displays the differential voltage. The rate of total energy change is a function of lithiation and delithiation and indicates the differential voltage of the material. The computation of the differential voltage is described above with reference to equation (1) as an example using LCO. The same procedure can be applied to other materials as well. The differential voltage, which varies according to the composition, is correlated with the nominal voltage and can be used to screen the chosen composition for a given nominal voltage. In one embodiment, the computation of the nominal voltage is described above with reference to Table A for the case of LCO. The same method can be used for other materials as well.

The last button in phase 2 is button 172, labeled "capacity", which determines and displays the specific capacity of the battery. The rate of total energy change as a function of lithiation and delithiation and the limit up to which the battery electrode material is stable upon delithiation, as determined by the simulations, is used to compute the intrinsic specific capacity (e.g., in mAh/g) of the material within given upper and lower cutoff voltages. In one embodiment, an upper cut-off voltage of 4.2V is used for capacity computations. In other embodiments, different upper cutoff voltages are possible to use in button 172 of phase 2. One embodiment for the fast estimation of the capacity is described above with reference to equation (2) for the case of LCO. The same method can be applied to other materials as well.

Phase 3 includes the selection of the hybrid model and computation of coin cell discharge rate behavior. Button 174 selects model 1, the hybrid half cell model described hereinabove. As discussed above, it is possible to use DFT quantum simulated data for the designed cathode active material with standard electrolyte and anode materials at the coin cell level to determine the discharge rate of the cell. If desired, additional models (e.g., models 2 and 3) can also be provided. In one embodiment, model 2 is the Nelson model and model 3 is the Freedom CAR model.

Buttons 176 and 178 use the hybrid model to calculate the coin cell 25 discharge rate behavior. The QS DFT simulated delithiated structures in phase 2 are used for simulating mobility or resistance of Li ion diffusion as a function of delithiation. This information is combined with the experimental resistance or mobility for the anode and the electrolyte to compute the low (e.g., 0.2 C) and high (e.g., IOC) discharge rate behavior of the chosen material. Button 176 calculates the 5 QM V(x) low and button 178 calculates the QM V(x) high.

Phase 4 is under the "Cylindrical" label and includes operations 180, 182, 184, 186, and 188.

Cell button 180 opens the Battery Design Studio (BDS) simulation tool. The Battery Design Studio (BDS) is a system level cell design software tool, which is commercially available from Battery Design, LLC of Yokohama Japan. BDS is just one example of the full cell system level design software and tools developed over years by universities, industry and government labs. Across the board, the BDS and other full cell system level design tools and software are based on the experimentally obtained discharge curves of the electrode materials. The software tools use experimentally obtained discharge curves of the given electrode material with a counter electrode and an electrolyte to design and simulate the performance of cylindrical or prismatic full cells. In one embodiment, the simulated half cell discharge curves of QM designed electrode materials are used with a given counter electrode and electrolyte, as described above with reference to the hybrid model and FIGS. 6A-6C. The results are fed as input to the BDS, or some other system level full cell design and evaluation tool. The use of the hybrid model together with software tools, such as BDS, allows the design, testing and evaluation of system level cylindrical or prismatic full cells with QM designed electrode material in a given counter electrode, electrolyte, separator, and balance of materials (BOM) for full cells. Button 182 calculates the design for the cylindrical full cells with BDS using the QM designed and simulated cathode material. The low rate (e.g., 0.2 C) discharge behavior of the chosen active material composition is used with standard binder, conductivity aid, electrolyte, and anode materials to design 18650 cylindrical cells with computed system level capacity and discharge characteristics.

Button 184 performs the testing of the cylindrical full cells designed in option 182. The charging and discharging behavior of the designed cell under user-defined procedures is tested by running the user-defined procedures. The procedures are generally specific to and explained in the BDS or other specific system level cylindrical or prismatic full cell design and evaluation tool or software. The results are displayed to the user.

Button 186 performs comparisons of the cylindrical cells. The charge and discharge behavior of the designed cell, with the chosen cathode material composition, is compared to the charging and discharging behavior of the similar size cell and other cathode material chemistries as described in the user-manual of BDS, or some other system level design tool, used for buttons 180-186. The results are presented on the display. Buttons listed under 190 are the same buttons under cylindrical batteries, except that they are applied to prismatic batteries.

Figure 12A:
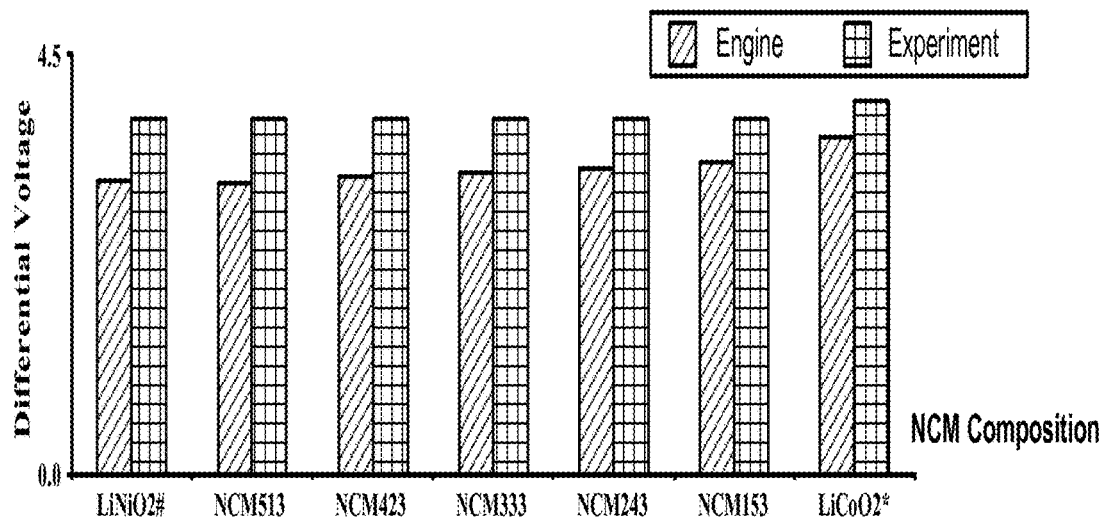
FIG. 12A charts a comparison between predicted values and experimental values for the differential voltage of different compositions.
Figure 12B:
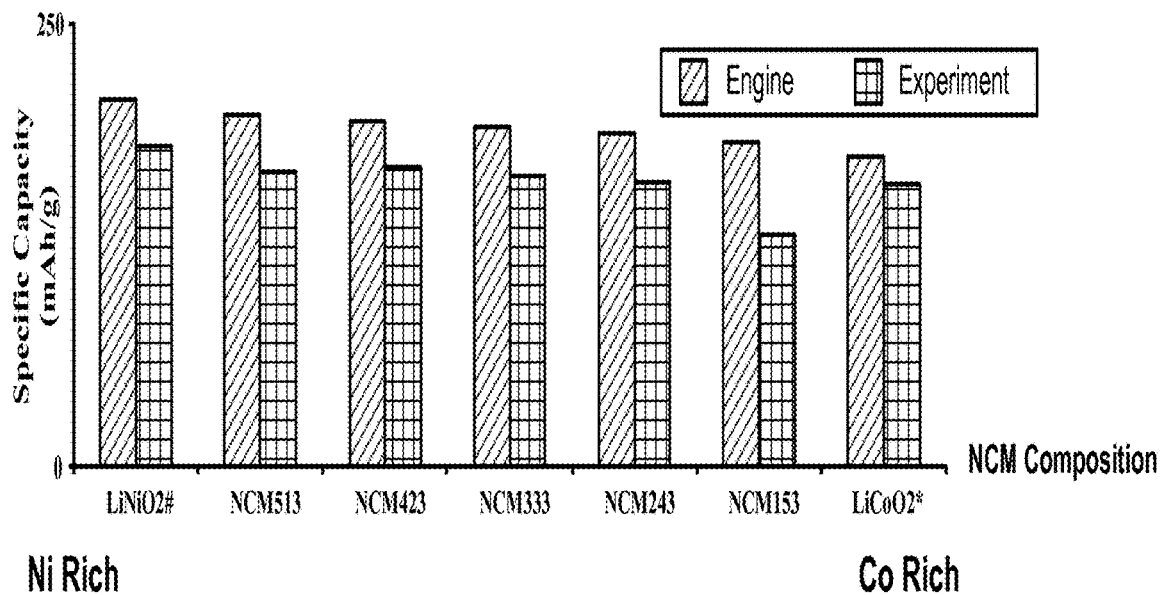
FIG. 12B presents a comparison of the experimentation results and the simulations results for the estimation of battery capacity.

FIG. 12A charts a comparison between predicted values and experimental values for the differential voltage of different compositions. Although the values are fairly close, the values obtained with the development engine were slightly (5-10%) smaller than the actual values obtained through experimentation. FIG. 12B presents a comparison for the estimation of battery capacity. In this case, the development engine predicted slightly higher values than those obtained through experimentation.

Figure 13:
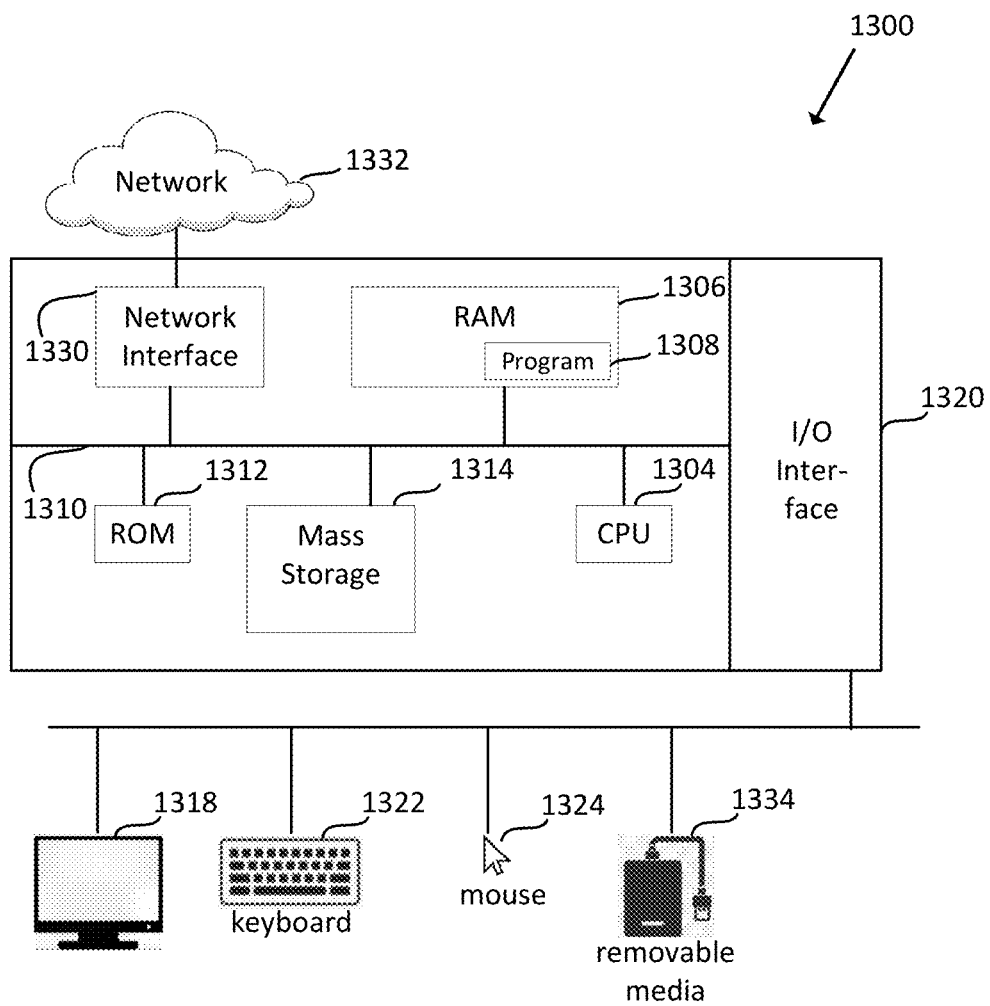
FIG. 13 depicts an exemplary computer environment for implementing embodiments of the invention.

FIG. 13 depicts an exemplary computer environment for implementing embodiments of the invention. It should be appreciated that the methods described herein may be performed with a digital processing system, such as a conventional, general-purpose computer system. Special purpose computers, which are designed or programmed to perform only one function, may be used in the alternative. The computer system includes a central processing unit (CPU) 1304, which is coupled through bus 1310 to random access memory (RAM) 1306, read-only memory (ROM) 1312, and mass storage device 1314. Development engine program 1308 resides in random access memory (RAM) 1306, but can also reside in mass storage 1314.

Mass storage device 1314 represents a persistent data storage device such as a floppy disc drive or a fixed disc drive, which may be local or remote. Network interface 1330 provides connections via network 1332, allowing communications with other devices. It should be appreciated that CPU 1304 may be embodied in a general-purpose processor, a special purpose processor, or a specially programmed logic device. Input/Output (I/O) interface provides communication with different peripherals and is connected with CPU 1304, RAM 1306, ROM 1312, and mass storage device 1314, through bus 1310. Sample peripherals include display 1318, keyboard 1322, cursor control 1324, removable media device 1334, etc.

Display 1318 is configured to display the user interfaces described herein, such as the GUI shown in FIG. 11. Keyboard 1322, cursor control 1324, removable media device 1334, and other peripherals are coupled to I/O interface 1320 in order to communicate information in command selections to CPU 1304. It should be appreciated that data to and from external devices may be communicated through I/O interface 1320. The invention can also be practiced in distributed computing environments where tasks are performed by remote processing devices that are linked through a wire-based or wireless network.

Embodiments of the present invention may be practiced with various computer system configurations including hand-held devices, microprocessor systems, microprocessor-based or programmable consumer electronics, minicomputers, mainframe computers and the like. The invention can also be practiced in distributed computing environments where tasks are performed by remote processing devices that are linked through a network.

With the above embodiments in mind, it should be understood that the invention can employ various computer-implemented operations involving data stored in computer systems. These operations are those requiring physical manipulation of physical quantities. Any of the operations described herein that form part of the invention are useful machine operations. The invention also relates to a device or an apparatus for performing these operations. The apparatus may be specially constructed for the required purpose, such as a special purpose computer. When defined as a special purpose computer, the computer can also perform other processing, program execution or routines that are not part of the special purpose, while still being capable of operating for the special purpose. Alternatively, the operations may be processed by a general purpose computer selectively activated or configured by one or more computer programs stored in the computer memory, cache, or obtained over a network. When data is obtained over a network the data maybe processed by other computers on the network, e.g., a cloud of computing resources.

One or more embodiments of the present invention can also be fabricated as computer readable code on a computer readable medium. The computer readable medium is any data storage device that can store data, which can be thereafter be read by a computer system. Examples of the computer readable medium include hard drives, network attached storage (NAS), read-only memory, random-access memory, CD-ROMs, CD-Rs, CD-RWs, magnetic tapes and other optical and non-optical data storage devices. The computer readable medium can include computer readable tangible medium distributed over a network-coupled computer system so that the computer readable code is stored and executed in a distributed fashion.

Although the method operations were described in a specific order, it should be understood that other housekeeping operations may be performed in between operations, or operations may be adjusted so that they occur at slightly different times, or may be distributed in a system which allows the occurrence of the processing operations at various intervals associated with the processing, as long as the processing of the overlay operations are performed in the desired way.

Although the foregoing invention has been described in some detail for purposes of clarity of understanding, it will be apparent that certain changes and modifications can be practiced within the scope of the appended claims. Accordingly, the present embodiments are to be considered as illustrative and not restrictive, and the invention is not to be limited to the details given herein, but may be modified within the scope and equivalents of the appended claims.

What is claimed is:

1. A method for selecting electrode materials for a lithium battery using a design engine, the method comprising:
    providing a database of structures of electrode materials and related properties which serve as building blocks for a battery electrode, wherein the structures comprise real structures, hypothetical structures or a combination thereof, and the structures include different types of structures comprising
        single type structures with one transition metal, wherein the single type structures include non-defected structures, defected structures which include user-created defects using the design engine, or a combination thereof,
        composite structures with two or more single structures which include any combination of non-defected and defected structures,
        compositional formulas representing each element of the structures, or a combination thereof;
    selecting, by the design engine, building blocks from the database based on inputs from a user for a target electrode composition for an electrode;
    developing, by the design engine, possible material models for the target electrode composition by combining the selected building blocks;
    estimating properties of at least one cell performance parameter;
    calculating a cell discharge rate behavior;
    selecting an electrode material composition based on the estimated properties and cell discharge rate behavior; and
    testing and validating different material compositions for the target electrode composition before selecting the electrode material composition.

2. The method as recited in claim 1, wherein developing possible material models further includes:
    selecting candidate material models of the target composition from the possible material models; and screening the candidate material models.

3. The method as recited in claim 2, wherein screening further includes:
    separating the candidate material models into groups for simulation of targeted performance characteristics.

4. The method as recited in claim 2 further includes:
    creating defects in a crystalline structure of the candidate material models using the design engine based on user input.

5. The method as recited in claim 2, wherein developing material models further includes:
    performing analysis of X-ray and neutron diffraction spectra of the candidate material models.

6. The method as recited in claim 1, wherein selecting building blocks from the database further includes:

selecting building blocks based on a target cathode composition, a target anode composition, or a target electrolyte composition;

selecting a type of lattice and selecting a type of composites made of more than one type of lattice;

selecting a number of building blocks in the material models and selecting the building blocks for the material models; and selecting a fractional composition for each of the building blocks in the material model.

7. The method as recited in claim 1, wherein estimating properties further includes:

estimating one or more properties selected from a group consisting of safety, cycling ability, volume change in charge and discharge, differential voltage, and capacity.

8. The method as recited in claim 1, wherein calculating a cell discharge rate behavior further includes:

selecting a hybrid model for a coin cell, the hybrid model combining quantum mechanical simulation data with data obtained via experimentation.

9. The method as recited in claim 8, wherein calculating a cell discharge rate behavior further includes:

calculating the coin cell discharge rate behavior using the hybrid model.

10. The method as recited in claim 1, wherein selecting electrode material composition further includes:

combining simulated discharge characteristics with user input on morphology, surface area, tap density, and lithium concentration to design full cells with required performance characteristics.

11. The method as recited in claim 1, wherein selecting the electrode material composition further includes:

invoking a cell system level design software tool stored in the computer system for designing, testing and evaluating the lithium battery with the selected electrode material composition.

12. A non-transitory computer-readable storage medium containing a computer program for selecting electrode materials for a lithium battery, the computer program, when executed by one or more processors, comprises:

developing possible material models based on user input for a target electrode composition of an electrode, wherein the user input includes structural lattice type, elements and composition formulas for the target electrode composition, the possible material models are developed for performing structural and energy analysis for battery stability, safety, cycling and performance, wherein developing the possible material models comprises, accessing a database containing structures of electrode materials and related properties which serve as building blocks for a battery electrode, wherein the structures comprise real structures, hypothetical structures or a combination thereof, and the structures include different types of structures comprising, single type structures with one transition metal, wherein the single type structures include non-defected structures, defected structures which include user-created defects, or a combination thereof, composite structures with two or more single structures which include any combination of non-defected and defected structures, compositional formulas representing each element of the structures, or a combination thereof;

selecting building blocks, and combining the building blocks to develop the possible material models;

estimating properties of at least one cell performance parameter;

calculating a cell discharge rate behavior;

selecting an electrode composition based on the estimated properties and cell discharge rate behavior; and performing testing and validating different material compositions for the target electrode composition before selecting the electrode material composition.

13. The non-transitory computer-readable medium as recited in claim 12, wherein developing possible material models further includes:

selecting candidate material models of the target composition from the possible material models; and screening the candidate material models.

14. The non-transitory computer-readable medium as recited in claim 13, wherein screening the candidate material models further includes:

separating the candidate material models into groups for simulation of targeted performance characteristics.

15. The non-transitory computer-readable medium as recited in claim 13, wherein selecting candidate material models further includes:

creating defects in a crystalline structure of the candidate material models using a design engine based on user input.

16. The non-transitory computer-readable medium as recited in claim 13, wherein developing possible material models further includes:

performing analysis of X-ray and neutron diffraction spectra of the candidate material models.

17. The non-transitory computer-readable medium as recited in claim 12, wherein selecting the building blocks from the database further includes:

selecting building blocks based on a target cathode composition, a target anode composition, or a target electrolyte composition;

selecting a type of lattice and selecting a type of composites made of more than one type of lattice;

selecting a number of the building blocks in the possible material models and selecting the building blocks for the possible material models; and selecting a fractional composition for each of the building blocks in the possible material models.

18. The non-transitory computer-readable medium as recited in claim 12, wherein estimating properties further includes:

for estimating one or more properties selected from a group consisting of safety, cycling ability, volume change in charge and discharge, differential voltage, and capacity.

* * * * *